(12) United States Patent
Ray et al.

(10) Patent No.: US 7,115,370 B2
(45) Date of Patent: Oct. 3, 2006

(54) COMBINATORIAL OLIGONUCLEOTIDE PCR

(75) Inventors: Jill M. Ray, Rockville, MD (US); Teri Heiland, New Market, MD (US); Indira Carey, Silver Spring, MD (US)

(73) Assignee: Capital Genomix, Inc., Gaithersburg, MD (US)

( * ) Notice: Subject to any disclaimer, the term of this patent is extended or adjusted under 35 U.S.C. 154(b) by 0 days.

(21) Appl. No.: 10/164,103

(22) Filed: Jun. 5, 2002

(65) Prior Publication Data

US 2006/0172289 A1    Aug. 3, 2006

(51) Int. Cl.
C12Q 1/68 (2006.01)
C12P 19/34 (2006.01)

(52) U.S. Cl. .......................................... 435/6; 435/91.2
(58) Field of Classification Search .................... 435/6, 435/91.2, 180, 172.3, 91.1, 183; 531/23.1, 531/24.3; 536/24.3, 25.3, 24.33, 23.1, 24.1
See application file for complete search history.

(56) References Cited

U.S. PATENT DOCUMENTS

| | | | |
|---|---|---|---|
| 4,865,707 A | 9/1989 | Karger et al. ............ 204/182.8 |
| 5,053,336 A | 10/1991 | Vanderlaan et al. .... 435/240.27 |
| 5,290,677 A | 3/1994 | Robertson et al. .............. 435/5 |
| 5,521,084 A | 5/1996 | Kowalski et al. ......... 435/240.2 |
| 5,650,274 A | 7/1997 | Kambara et al. ............... 435/6 |
| 5,656,470 A | 8/1997 | Martinis et al. ............ 435/183 |
| 5,688,648 A | 11/1997 | Mathies et al. ................ 435/6 |
| 5,736,330 A | 4/1998 | Fulton ............................ 435/6 |
| 5,759,781 A | 6/1998 | Ward et al. ..................... 435/6 |
| 5,767,288 A | 6/1998 | Rock et al. .................... 549/22 |
| 5,770,716 A | 6/1998 | Khan et al. ................. 536/23.1 |
| 5,804,380 A | 9/1998 | Harley et al. ................... 435/6 |
| 5,817,462 A | 10/1998 | Garini et al. ................... 435/6 |
| 5,830,657 A | 11/1998 | Leushner et al. ............... 435/6 |
| 5,837,836 A | 11/1998 | Friderici et al. ........... 536/23.1 |
| 5,843,773 A | 12/1998 | Shin et al. ............... 435/320.1 |
| 5,851,772 A | 12/1998 | Mirzabekov et al. .......... 435/6 |
| 5,853,990 A | 12/1998 | Winger et al. |
| 5,853,992 A | 12/1998 | Glazer et al. ................... 435/6 |
| 5,866,330 A | 2/1999 | Kinzler et al. ................. 436/6 |
| 5,871,697 A * | 2/1999 | Rothberg et al. .......... 422/68.1 |
| 5,874,215 A | 2/1999 | Kuiper et al. ................... 435/6 |
| 5,922,535 A | 7/1999 | Huo ............................... 435/6 |
| 5,945,290 A | 8/1999 | Cowsert ......................... 435/6 |
| 5,955,276 A * | 9/1999 | Morgante et al. .............. 435/6 |
| 6,002,817 A | 12/1999 | Kopelman et al. ............ 385/12 |
| 6,007,996 A | 12/1999 | McNamara et al. ........... 435/6 |
| 6,045,994 A * | 4/2000 | Zabeau et al. ................. 435/6 |
| 6,068,843 A | 5/2000 | Duhamel et al. ......... 424/184.1 |
| 6,090,572 A | 7/2000 | Crosby ......................... 435/29 |
| 6,139,800 A | 10/2000 | Chandler ................. 422/82.08 |

(Continued)

OTHER PUBLICATIONS

Wang et al (Proc. Natl. Acad. Sci. (1991) 88:11505-11509).*

(Continued)

*Primary Examiner*—Jeffrey Fredman
(74) *Attorney, Agent, or Firm*—Fulbright & Jaworski L.L.P.

(57) ABSTRACT

The present invention is directed to a method of detecting gene expression and analysis of both known and unknown genes. In the method utilizing combinatorial oligonucleotide PCR™, no single molecular species of DNA gives rise to more than one fragment in a collection of products which are subsequently amplified and representative of each expressed gene. More specifically, the present invention improves known methods by eliminating the recovery of restriction fragments with two identical ends and furthermore regards amplification and isolation of the restriction fragment utilizing a labeled primer.

70 Claims, 4 Drawing Sheets

U.S. PATENT DOCUMENTS

| | | | |
|---|---|---|---|
| 6,177,247 B1 | 1/2001 | Mathies et al. | 435/6 |
| 6,221,600 B1* | 4/2001 | MacLeod et al. | 435/6 |
| 6,232,067 B1* | 5/2001 | Hunkapiller et al. | 435/6 |
| 6,238,869 B1* | 5/2001 | Kris et al. | 435/6 |
| 6,261,782 B1 | 7/2001 | Lizardi et al. | 435/6 |
| 6,262,334 B1 | 7/2001 | Endege et al. | 800/8 |
| 6,280,949 B1 | 8/2001 | Lizardi | 435/6 |
| 6,310,193 B1 | 10/2001 | Black et al. | 536/23.5 |
| 6,316,190 B1 | 11/2001 | Rein et al. | 435/6 |
| 6,329,140 B1 | 12/2001 | Lockhart et al. | 435/6 |
| 6,383,754 B1 | 5/2002 | Kaufman et al. | 435/6 |
| 6,521,428 B1 | 2/2003 | Senapathy | 435/91.2 |
| 6,677,121 B1 | 1/2004 | Lizardi et al. | 435/6 |

OTHER PUBLICATIONS

Song and Osborn, "A method for examining expression of homologous genes in plant polyploids." *Plant Mol Biol.* 26:1065-1071, 1994.

Stone and Wharton, "Targeted RNA fingerprinting: the cloning of differentially-expressed cDNA fragments enriched for members of the zinc finger gene family." *Nucleic Acids Res.,* 22:2612-2618, 1994.

Velculescu et al, "Characterization of the yeast transcriptome." *Cell,* 88:243-251, 1997.

Velculescu et al., "Serial analysis of gene expression." *Science,* 270:484-487, 1995.

Vos et al., "AFLP: a new technique for DNA fingerprinting," *Nucleic Acids Research.* 23 4407-4414, 1995.

Wang and Feuerstein, "Direct Sequencing of DNA isolated from mRNA differential display." *Biotechniques,* 18:448-453, 1995.

Wang et al., "Rapid analysis of gene expression (RAGE) facilitates universal expression profiling," *Nucleic Acids Research,* 27(23):4609-4618, 1999.

Zhang et al., "Gene expression profiles in normal and cancer cells," *Science,* 276:1268-1272, 1997.

Ivanova and Belyavsky. Identification of differentially expressed genes by restriction endonuclease-based gene expression fingerprinting, 23:2954-2958, 1995.

Jiang et al., "RaSH. a rapid subraction hybidization approach for identifying and cloning differentially expressed genes." *Proc. Natl. Acad. Sci., USA,* 97:12684-12689, 2000.

Kornmann et al., "Analysis of circadian liver gene expression by ADDER, a highly sensitive method for the display of differentially expressed mRNAs." *Nucleic Acids Research,* 29;e51. 10 pages, 2001.

Liang and Pardee. "Differential display of eukaryotic messenger RNA by means of the polymerase chain reaction." *Science,* 257:967-971, 1992.

MacLeod et al., "Binding of the transcription factor, Sp1, to non-target sites in DNA modified by benzo[α]pyrene diol epoxide," *Carcinogenesis* 16:975-983, 1995.

MacLeod et al., "Interference of benzo[α]pyrene Diol epoxide-deoxyguanosine adductsin a GC box with binding of the transcription factor Sp1." *Mol. Carcinogenesis* 16:44-52, 1996.

MacLeod, "A possible role in chemical carcinogenesis for epigenetic, heritable changes in gene expression," *Mol. Carcinogenesis* 15:241-250, 1996.

Money et al., "AFLP-based mRNA fingerprinting." *Nucleic Acids Research,* 24:2616-2617, 1996.

Okubo et al., "Large scale cDNA sequencing for analysis o quantitative and qualitative aspects of gene expression." *Nat Genet..* 2:173-179, 1992.

Pierce et al. "Deregulated expression of E2F1 induces hyperplasia and cooperates with ras in skin tumor development." *Oncogene.* 16:1267-1276, 1998.

Pierce et al., "Increased E2F1 activity induces skin tumors in mice heteroxygous and nullizygous for p53." *Proc. Natl Acad. Sci. USA.* 95:8858-8863, 1998.

Schena et al., "Quantitative monitoring of gene expression patterns with a complementary DNA microarray," *Science,* 270:467-470, 1995.

Schibler et al., "The isolation of differentially expressed mRNA sequences by selective amplification via biotin and restriction-mediated enrichment," *Methods,* 24:3-14, 2001.

Shinkers et al. Nature Biotechnology—17: 798-803 (1999).

Adams et al., "Rapid cDNA sequencing (expressed sequence tags) from a directionally cloned human infant brain cDNA library," *Nat Genet.* 4:373-80, 1993.

An et al., "Organization and nucleotide sequence of a new ribosomal operon in *Escherichia coli* containing the genes for ribosomal protein S2 and clongation factor Ts." *Nucleic Acids Research,* 9:4163-4172. 1981.

Arrand et al., "Molecular cloning of the complete Epstein-Barr virus genome as a set of overlapping restriction endonuclease fragments," *Nucleic Acids Research,* 9:2999-3014, 1981.

Bachem et al., "Visualization of differential gene expression using a novel method of RNA fingerprinting based on AFLP: analysis of gene expression during potato tuber development." *The Plant Journal.* 9:745-753, 1996.

Bertioli et al., "An analysis of differential display shows a strong bias towards high copy number mRNAs." *Nucleic* Acids Res., 23:4520-3, 1995.

Boehringer Manheim, Biochemicals Catalog, Nucleic Acid Labeling and Detection, 1997.

Chen et al., "Gene expression profiling using a novel method: amplified differential gene expression (ADGE)," *Nucleic Acids Research.* 29(10):E46. 2001.

DeRisi et al., "Use of a cDNA micoarray to analyse gene expression patterns in human cancer." *Nature Genetics,* 14:457-460, 1996.

Habu et al., "Amplified Restriction Fragment Length Polymorphism-based mRNA fingerprinting using a single restriction enzyme that recognizes a 4-bp sequence." *Biochemical and Biophysical Research Communications.* 234:516-521. 1997.

Hedrick et al., "Sequence relationships between putative T-cell receptor polypeptides and immunoglobulins." *Nature.* 308:153-1588 1984.

Higuchi et al., "Kinetic PCR analysis: real-time monitoring of DNA amplification reactions." *BioTechnology.* 11:1026-1030, 1993.

Hsieh et al.. E2F1-induced apoptosis requires DNA binding but not transactivation and isinhibited by the retinoblastoma protein through directinteraction. *Genes Dev.,* 11:1840-1852. 1997.

Ito et al.. Flourescent differential display: arbitrarily primed RT-PCR fingerprinting on an Automated DNA sequencer: Febs letters 351: 231-236 (1994).

* cited by examiner

A.

B.

C.

D.

A.

B.

SEQUENCE LISTING

```
<160> NUMBER OF SEQ ID NOS: 26

<210> SEQ ID NO 1
<211> LENGTH: 12
<212> TYPE: DNA
<213> ORGANISM: Artificial Sequence
<220> FEATURE:
<223> OTHER INFORMATION: Primer

<400> SEQUENCE: 1
gctgtctaga cg                                                         12

<210> SEQ ID NO 2
<211> LENGTH: 12
<212> TYPE: DNA
<213> ORGANISM: Artificial sequence
<220> FEATURE:
<223> OTHER INFORMATION: Primer

<400> SEQUENCE: 2
cggtgatgca tc                                                         12

<210> SEQ ID NO 3
<211> LENGTH: 12
<212> TYPE: DNA
<213> ORGANISM: Artificial Sequence
<220> FEATURE:
<223> OTHER INFORMATION: Linker

<400> SEQUENCE: 3
cgtctagaca gc                                                         12

<210> SEQ ID NO 4
<211> LENGTH: 16
<212> TYPE: DNA
<213> ORGANISM: Artificial sequence
<220> FEATURE:
<223> OTHER INFORMATION: Linker

<400> SEQUENCE: 4
gctgtctaga cgcatg                                                     16

<210> SEQ ID NO 5
<211> LENGTH: 12
<212> TYPE: DNA
<213> ORGANISM: Artificial sequence
<220> FEATURE:
<223> OTHER INFORMATION: Linker

<400> SEQUENCE: 5
```

```
cggtgatgca tc                                                      12
```

```
<210> SEQ ID NO 6
<211> LENGTH: 16
<212> TYPE: DNA
<213> ORGANISM: Artificial sequence
<220> FEATURE:
<223> OTHER INFORMATION: Linker

<400> SEQUENCE: 6
gatcgatgca tcaccg                                                  16

<210> SEQ ID NO 7
<211> LENGTH: 19
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(19)
<223> OTHER INFORMATION: n equals any nucleotide

<400> SEQUENCE: 7
gcgtctagac gcatgnnnn                                               19

<210> SEQ ID NO 8
<211> LENGTH: 19
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(19)
<223> OTHER INFORMATION: n equals any nucleotide

<400> SEQUENCE: 8
cggtgatgca tcgatcnnn                                               19

<210> SEQ ID NO 9
<211> LENGTH: 11
<212> TYPE: DNA
<213> ORGANISM: Artificial Sequence
<220> FEATURE:
<223> OTHER INFORMATION: restriction enzyme sites
<220> FEATURE:
<221> NAME/KEY: misc_feature
<222> LOCATION: (1)..(11)
<223> OTHER INFORMATION: N equals any nucleotide

<400> SEQUENCE: 9
gacnnnnngt c                                                       11

<210> SEQ ID NO 10
<211> LENGTH: 13
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(13)
<223> OTHER INFORMATION: N equals any nucleotide
<220> FEATURE:
<221> NAME/KEY: misc_feature
<222> LOCATION: (11)..(11)
<223> OTHER INFORMATION: Y equals a pyrimidine

<400> SEQUENCE: 10
```

-continued

```
nacnnnngta ycn                                                                  13

<210> SEQ ID NO 11
<211> LENGTH: 12
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(12)
<223> OTHER INFORMATION: N equals any nucleotide

<400> SEQUENCE: 11
cgannnnnnt gc                                                                   12

<210> SEQ ID NO 12
<211> LENGTH: 11
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(11)
<223> OTHER INFORMATION: N equals any nucleotide

<400> SEQUENCE: 12
gccnnnnngg c                                                                    11

<210> SEQ ID NO 13
<211> LENGTH: 10
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(10)
<223> OTHER INFORMATION: N equals any nucleotide

<400> SEQUENCE: 13 gatnnnnatc                                                                      10

<210> SEQ ID NO 14
<211> LENGTH: 11
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(11)
<223> OTHER INFORMATION: N equals any nucleotide

<400> SEQUENCE: 14
ccnnnnnnng g                                                                    11

<210> SEQ ID NO 15
<211> LENGTH: 11
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(11)
<223> OTHER INFORMATION: N equals any nucleotide
```

-continued

```
<400> SEQUENCE: 15
gcannnnntg c                                                        11

<210> SEQ ID NO 16
<211> LENGTH: 12
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(12)
<223> OTHER INFORMATION: N equals any nucleotide

<400> SEQUENCE: 16
ccannnnnnt gg                                                       12

<210> SEQ ID NO 17
<211> LENGTH: 12
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(12)
<223> OTHER INFORMATION: N equals any nucleotide

<400> SEQUENCE: 17
gacnnnnnng tc                                                       12

<210> SEQ ID NO 18
<211> LENGTH: 11
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(11)
<223> OTHER INFORMATION: N equals any nucleotide

<400> SEQUENCE: 18
cctnnnnnag g                                                        11

<210> SEQ ID NO 19
<211> LENGTH: 10
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(10)
<223> OTHER INFORMATION: N equals any nucleotide

<400> SEQUENCE: 19 gagtcnnnnn                                                          10

<210> SEQ ID NO 20
<211> LENGTH: 10
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(10)
<223> OTHER INFORMATION: N equals any nucleotide
```

```
<220> FEATURE:
<221> NAME/KEY: misc_feature
<222> LOCATION: (3)..(3)
<223> OTHER INFORMATION: Y equals pyrimidine
<220> FEATURE:
<221> NAME/KEY: misc_feature
<222> LOCATION: (8)..(8)
<223> OTHER INFORMATION: R equals either an A or G

<400> SEQUENCE: 20 caynnnnrtg                                                                  10

<210> SEQ ID NO 21
<211> LENGTH: 11
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(11)
<223> OTHER INFORMATION: N equals any nucleotide

<400> SEQUENCE: 21
gcnnnnnnng c                                                                11

<210> SEQ ID NO 22
<211> LENGTH: 11
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(11)
<223> OTHER INFORMATION: N equals any nucleotide

<400> SEQUENCE: 22
ccannnnntg g                                                                11

<210> SEQ ID NO 23
<211> LENGTH: 10
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(10)
<223> OTHER INFORMATION: N equals any nucleotide

<400> SEQUENCE: 23 gacnnnngtc                                                                  10

<210> SEQ ID NO 24
<211> LENGTH: 13
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(13)
<223> OTHER INFORMATION: N equals any nucleotide

<400> SEQUENCE: 24
ggccnnnnng gcc                                                              13

<210> SEQ ID NO 25
```

```
-continued
<211> LENGTH: 15
<212> TYPE: DNA
<213> ORGANISM: Artificial Sequence
<220> FEATURE:
<223> OTHER INFORMATION: Restriction Enzyme Sites
<220> FEATURE:
<221> NAME/KEY: misc_feature
<222> LOCATION: (1)..(15)
<223> OTHER INFORMATION: N equals any nucleotide

<400> SEQUENCE: 25 ccannnnnn nntgg                                                                   15

<210> SEQ ID NO 26
<211> LENGTH: 10
<212> TYPE: DNA
<213> ORGANISM: Artificial Sequence
<220> FEATURE:
<223> OTHER INFORMATION: Restriction Enzyme Site
<220> FEATURE:
<221> NAME/KEY: misc_feature
<222> LOCATION: (1)..(10)
<223> OTHER INFORMATION: N equals any nucleotide

<400> SEQUENCE: 26 gaannnnttc                                                                        10
```

COMBINATORIAL OLIGONUCLEOTIDE PCR

FIELD OF THE INVENTION

Generally, the present invention is directed to the fields of genomics and molecular biology. In particular, the present invention is directed to the field of gene expression and analysis of both known and unknown genes. Specifically, the present invention regards global monitoring of gene expression utilizing combinatorial oligonucleotide polymerase chain reaction. More specifically, the present invention is directed to improvements for combinatorial oligonucleotide polymerase chain reaction comprising amplifiable fragments having non-identical ends and linkers comprising an isolation moiety.

BACKGROUND OF THE INVENTION

The degree of differentiation or physiological state of a cell, a tissue or an organism is characterized by a specific expression status, i.e., the degree of transcriptional activation of all genes or particular groups of genes. The molecular basis for numerous biological processes that result in a change in this state is the coordinated transcriptional activation or inactivation of particular genes or groups of genes in a cell, an organ or an organism. Characterization of this expression status is of key importance for answering many biological questions. Changes in gene expression in response to a stimulus, a developmental stage, a pathological state or a physiological state are important in determining the nature and mechanism of the change and in finding cures that could reverse a pathological condition. Patterns of gene expression are also expected to be useful in the diagnosis of pathological conditions, and for example, may provide a basis for the subclassification of functionally different subtypes of cancerous conditions.

Several methods that can analyze the expression status of genes are known in the art. Differential display RT-PCR™ (DDRT) is one method for analyzing differential gene expression in which subpopulations of complementary DNA (cDNA) are generated by reverse transcription of mRNA by using a cDNA primer with a 3' extension (preferably two bases). Random 10 base primers are then used to generate PCR™ products of transcript-specific lengths. If the number of primer combinations used is large enough, it is statistically possible to detect almost all transcripts present in any given sample. PCR™ products obtained from two or more samples are then electrophoresed next to one another on a gel and differences in expression are directly compared. Differentially expressed bands can be cut out of the gel, reamplified and cloned for filter analysis.

It is possible to enrich the PCR™ (polymerase chain reaction) amplification products for a particular subgroup of all mRNA molecules, e.g., members of a particular gene family, by using one primer which has a sequence specific for a gene family in combination with one of the 10 base random primers. This technique of DDRT is described (Liang and Pardee, 1992; Liang et al., 1993; Bauer et al., 1993; Stone and Wharton, 1994; Wang and Feuerstein, 1995; WO 93/18176; and DE 43 17 414).

There are a number of disadvantages to the experimental design of DDRT. The differential banding patterns are often only poorly reproducible. Due to the design of the primers even the use of longer random primers of, e.g., 20 bases in length does not satisfactorily solve the problem of reproducibility (Ito et al., 1994). In order to evaluate a significant portion of differentially expressed genes, a large number of primer combinations must be used and multiple replicates of each study must be done. The method often results in a high proportion of false positive results and rare transcripts cannot be detected in many DDRT studies (Bertioli et al., 1995.)

Due to the non-stringent PCR™ conditions and the use of only one arbitrary primer further analysis by sequencing is necessary to identify the gene. Sequencing of selected bands is problematic since the same primer often flanks DDRT products at both ends so that direct sequencing is not possible and an additional cloning step is necessary. Due to the use of short primers, a further reamplification step with primer molecules extended on the 5' side is necessary even if two different primers flank the product. Finally, due to the use of random primers, it is never quite possible to be sure that the primer combinations recognize all transcripts of a cell. This applies, even when using a high number of primers, to studies which are intended to detect the entirety of all transcripts as well as to studies which are directed towards the analysis of a subpopulation of transcripts such as a gene family (Bertioli et al., 1995).

A variant of DDRT, known as GeneCalling, has been described (Shimkets et al., 1999) which addresses some of these problems. In this method, multiple pairs of restriction endonucleases are used to prepare specific fragments of a cDNA population prior to amplification with pairs of universal primers. This improves the reproducibility of the measurements and the false positive rate, but the patterns are very complex and identification of individual transcripts requires the synthesis of a unique oligonucleotide for each gene to be tested. In addition, the quantitative data obtained are apparently significant only for changes above 4-fold (Shimkets et al., 1999) and only a weak correlation with other techniques is obtained. The ability of the technique to distinguish the gene-specific band from the complex background for any arbitrarily chosen gene has not been documented (Shimkets et al., 1999).

AFLP based mRNA fingerprinting further addresses some of the deficiencies of DDRT. AFLP allows for the systematic comparison of the differential expression of genes between RNA samples (Habu, 1997). The technique involves the endonuclease digestion of immobilized cDNA by a single restriction enzyme. The digested fragments are then ligated with a linker specific for the restriction cut site. The tailed fragments are subsequently amplified by PCR™ employing primers complementary to the linkers added to the digest with the addition of variable nucleotides at the 3' end of the primers. The products of the amplification are visualized by PAGE and banding patterns compared to reveal differences in RNA transcription patterns between samples. Although based RNA fingerprinting provides an indication of the RNA message present in a given sample, it fails to restrict the potential number of signals produced by each individual RNA strand. With this technique, each RNA strand may potentially produce multiple fragments and therefore multiple signals upon amplification. This failure to restrict the number of signals from each message complicates the results that must be evaluated.

Song and Osborn (1994) describe a method for examining the expression of homologous genes in plant polyploids in which the techniques of RT-PCR™ and RFLP (restriction fragment length polymorphism) analysis are combined with one another. In this method a cDNA is produced from RNA by reverse transcription, then amplified by using two gene-specific primers. The amplification products are transcript-specifically shortened by endonuclease cleavage, separated by electrophoresis according to their length, cloned, and then analyzed by sequencing. This method has the disadvantage of low sensitivity, as a cloning step is necessary to characterize the expression products. A further disadvantage of this method is that gene specific sequence information must be available on at least two regions within the analyzed genes in order to design suitable primers.

In principle, gene expression data for a particular biological sample could be obtained by large-scale sequencing of a cDNA library. The role of sequencing cDNA, generated by reverse transcription from mRNA, has been debated for its value in the human genome project. Proponents of genomic sequencing have argued the difficulty of finding every mRNA expressed in all tissues, cell types, and developmental stages. It is also believed that cDNA libraries do not provide all sequences corresponding to structural and regulatory polypeptides (Putney et al., 1983). In addition, libraries of cDNA may be dominated by repetitive elements, mitochondrial genes, ribosomal RNA genes, and other nuclear genes comprising common or housekeeping sequences. While some mRNAs are abundant, others are rare, resulting in cellular quantities of mRNA from various genes that can vary by several orders of magnitude. Therefore, sequencing of transcribed regions of the genome using cDNA libraries has been considered unsatisfactory.

Techniques based on cDNA subtraction or differential display can be used to compare gene expression patterns between two cell types (Hedrick et al., 1984; Liang and Pardee, 1992), but provide only a partial analysis, with no quantitative information regarding the abundance of messenger RNA. Expressed sequence tags (ESTs) have been valuable for gene discovery (Adams et al., 1993; Okubo et al., 1992), but like Northern blotting, RNase protection, and reverse transcriptase-polymerase chain reaction (RT-PCR™) analysis (Alwine et al., 1977; Zinn et al, 1983; Veres et al., 1987) the approach only evaluates a limited number of genes at a time.

In Chen et al. (2001), amplified differential gene expression (ADGE) is used to quadratically amplify the ratio of a gene in two samples before displaying them. This amplification does not alter the ratio of expression of genes that are expressed at the same level, but quadratically increases the ratio for those with different expression levels. It is used to reveal gene expression profiles between two samples and may be used to perform global analysis. The technique requires hybridization and addition of separate adaptors to the tester and driver cDNAs. Jiang et al. (2000) describe Rapid Subtraction Hybridization (RaSH) as involving enzymatically digesting cDNA into small fragments, ligating to adaptors, PCR amplifying and then incubating with tester and driver PCR fragments. The key component of this technique is subtractive hybridization, and multiple fragments are recovered from a single cDNA species. Reciprocal subtraction differential RNA display (RSDD) combines reciprocal subtraction of cDNA libraries followed by differential RNA display (Kang, et al. 1998). The approach results in the enrichment of unique sequences and reduction of common sequences. All of these techniques require cloning and sequencing to identify differences in gene expression.

Serial analysis of gene expression (SAGE) (U.S. Pat. No. 5,866,330; Kinzler et al., 1995) was developed for global gene expression analysis. It is based on the use of short (i.e. 9–10 base pair) nucleotide sequence tags that identify a defined position in an mRNA and are used to ascertain the identity of the corresponding transcript and gene. The cDNA tags are generated from mRNA samples, randomly paired, concatenated, cloned, and sequenced. While this method allows the analysis of a large number of transcripts, the identification of individual genes requires sequencing of tens of thousands of tags for comparison of even a small number of samples. Although SAGE provides a comprehensive picture of gene expression, it cannot be specifically directed at a small subset of the transcriptome (Zhang et al., 1997; Velculescu et al., 1995). Data on the most abundant transcripts is the easiest and fastest to obtain, while about a megabase of sequencing data is needed for confident analysis of low abundance transcripts.

Microarray technology utilizes hybridization of cDNAs or mRNAs to microarrays containing hundreds or thousands of individual cDNA fragments or oligonucleotides specific for particular genes or ESTs. The matrix for hybridization is either a DNA chip, a slide or a membrane. This method can be used to direct a search towards specific subsets of genes, but cannot be used to identify novel genes. In addition, arrays are expensive to produce (DeRisi et al., 1996; Schena et al., 1995). For those methods using cDNA arrays, a library of individually cloned DNA fragments must be maintained with at least one clone for each gene to be analyzed. Because much of the expense of utilizing microarrays lies in maintaining the fragment libraries and programming equipment to construct the microarray, it is only cost-efficient to produce large numbers of identical arrays. Data interpretation between experiments and laboratories have been problematic as data derived from arrayed elements are not directly comparable (Lakhani and Ashworth, 2001). Either SAGE and microarray technologies lack the flexibility to easily change the subset of the transcriptome being analyzed or to focus on smaller subsets of genes for more detailed analyses. Hybridization methods are also limited by lack of detection of genes not represented in ESTs.

Kornmann et al. (2001) describes amplification of double-stranded cDNA end restriction fragments (ADDER). cDNA is synthesized using an oligo dT containing two restriction sites and a biotin moiety. The 3' most cDNA fragment from each gene is recovered by digestion with a 4-base recognition restriction enzyme and recovered using SA-magnetic beads. An adaptor is ligated to the 5' end of the restriction fragment. The fragment is released from the oligo dT by restriction with AscI. A master cDNA stock is generated using universal primers. Differential display touchdown PCR is then carried out with 16 upstream and 12 downstream primers. The process uses radioisotopes and sequencing gels. The number of PCR products generated per reaction is greater than methods described herein, which makes results more difficult to interpret. In addition, no software exists to predict or aid in identification of the PCR product. Therefore, each differentially expressed PCR product must be cloned and sequenced.

As described above, current techniques for analysis of gene expression either monitor one gene at a time, are designed for the simultaneous and therefore more laborious analysis of thousands of genes or do not adequately restrict the signal to message ratio. There is a need for improved methods which encompass both rapid, detailed analysis of global expression patterns of genes as well as expression patterns of defined sets of genes for the investigation of a variety of biological applications. This is particularly true for establishing changes in the pattern of gene expression in the same cell type, for example, in different developmental stages, under different physiologic or pathologic conditions, when treated with different pharmaceuticals, mutagens, carcinogens, etc. Identification of differential patterns of expression has several utilities, including the identification of appropriate therapeutic targets, candidate genes for gene therapy (including gene replacement), tissue typing, forensic identification, mapping locations of disease-associated genes, and for the identification of diagnostic and prognostic indicator genes.

U.S. Pat. No. 6,221,600 and Wang et al. (2001) describe a combinatorial oligonucleotide PCR method for global gene expression, wherein a cDNA gives rise to no more than one fragment in a collection of products, which is subsequently amplified and therefore representative of each expressed gene. In these methods, artifactual amplification of multiple fragments from the same cDNA can occur during PCR by priming with a single primer.

The object of the present invention is to provide a method for gene expression analysis which exceeds the capabilities of the state of the art. Thus, the present invention described herein provides novel improvements to the art of gene expression analysis, particularly using combinatorial oligonucleotide polymerase chain reaction with labeled linkers and amplification of restriction fragments comprising non-identical ends.

SUMMARY OF THE INVENTION

In the present disclosure, a method has been developed which allows for the determination of changes in gene expression in multiple genes, known and unknown, in a rapid, quantitative and cost-effective fashion. This invention improves on the combinatorial oligonucleotide polymerase chain reaction technology, particularly which is described in U.S. Pat. No. 6,221,600, which is used to determine the differential expression of mRNA from cells or tissue. The methods described herein have the capability for detecting the frequency distribution of all polyadenylated mRNAs in a sample at any selected time. The invention reduces the complexity of analysis by ensuring that only a single unique fragment is derived from each molecular species of polyadenylated mRNA. Either the entire genome or a subset can be analyzed, and a single set of reagents and reaction conditions is sufficient for analysis of the complete genome. The technique allows for multiple samples to be analyzed simultaneously. The results generated from this invention are quantitative and proportional to the level of expression of the particular gene.

A unique feature of this method that distinguishes it from all DDRT methods is that a one-to-one correspondence exists between each molecular species of polyadenylated RNA and a PCR product of a particular length derived with a particular pair of PCR primers. Knowledge of a gene sequence therefore can be used to select the correct pair of primers to use for amplification and to predict the length of the corresponding product. This feature is also advantageous when combinatorially surveying the entire (genome) transcriptome. The length of the amplimer products, along with the information on the primers can be plugged into the database to identify the differentially expressed genes.

The present invention improves on combinatorial oligonucleotide polymerase chain reaction technology by facilitating the recovery of only one unique restriction fragment of each cDNA species in a collection of products. The invention utilizes an anchorable moiety to eliminate the recovery of rare restriction fragments with two identical ends that result upon restriction digestion with the second restriction enzyme. Failure to remove fragments with two identical ends would result in undesirable background upon subsequent amplification steps. Only the fragments comprising two nonidentical ends are isolated from other fragments via an anchorable linker, such as a biotinylated linker. This improvement dramatically improves the signal to noise ratio by eliminating amplification of templates that only contain identical ends. Use of the anchorable linker also facilitates improved recovery of the desired restriction fragments through specific, high affinity binding of biotin to streptavidin. The present invention also is directed to the compositions generated by the methods described herein. In a specific embodiment, a composition is a linker-ligated fragment from a DNA, such as a cDNA, referred to as a RAGEtag.

One embodiment of the invention involves a method comprising obtaining DNA molecules, which includes an anchorable moiety, and cleaving the DNA molecules with a first restriction endonuclease. The immobilized fragments are then digested with a second restriction endonuclease, cleaving the fragment from the anchor. The released fragments are then precipitated with carboxyl-magnetic beads and released from the beads. On occasion more than one restriction fragment from a single molecule of DNA may result from the second restriction digestion. Only the restriction fragments with two non-identical ends are desired. Two distinct linkers are then ligated to the non-identical cut ends of the DNA fragments. The linker that attaches to the fragments generated from the first restriction enzyme digestion has an anchorable moiety. After ligation of the linkers the desired fragments containing non-identical ends are isolated by immobilizing those fragments on the anchor via the anchorable moiety. The fragment library is then amplified. The order of the restriction digests may be reversed, thereby representing a more complete share of the DNA present in the sample. When the order of the restriction enzymes is reversed, the linker that has the anchorable moiety should also be switched.

It is envisioned that the methods of the present invention may be utilized to analyze specific DNA, be it genomic, non-genomic, cellular, mitochondrial DNA, cDNA or synthetic DNA. Where the DNA is cDNA, the initial immobilization of the DNA may take place prior to the reverse transcription of mRNA to cDNA, or the molecule may be subsequently immobilized. In another embodiment, the initial immobilization of the DNA may take place subsequent to the first restriction digestion. In a further embodiment, the initial immobilization of the DNA may take place subsequent to the first restriction digestion and linker ligation. For the initial immobilization it is envisioned that the DNA molecule may be immobilized at its 5' end or its 3' end.

It is envisioned in some embodiments that immobilization will occur at the anchorable moiety via a means of adhering. The means of adhering may facilitate either a covalent or non-covalent interaction. It is envisioned that the anchorable moiety may be located at either the 5' or 3' end of the DNA. It is envisioned that the means of adhering may be by well known in the art, such as biotin or an antibody.

In a further embodiment of the invention, mRNA is reverse transcribed to cDNA with an oligo-dT primer. It is further envisioned that reverse transcription may also be initiated at a random hexamer. The oligo-dT primer may be attached to a ligand, for example biotin or an antibody. Where the oligo-dT includes a ligand, it is envisioned that this ligand is the means through which the cDNA is immobilized to a substrate. Where the ligand is biotin, the biotin may be attached to streptavidin.

In another embodiment, the initial immobilization of the DNA may take place subsequent to the initial restriction digestion. It is envisioned that the immobilization will occur at the anchorable moiety via a means of adhering. The means of adhering may facilitate either a covalent or non-covalent interaction. It is envisioned that the anchorable moiety may be located at either the 5' or 3' end of the DNA. It is envisioned that the means of adhering may be either biotin or an antibody.

In a preferred embodiment of the invention, at least one linker is attached to one end of a fragment from the cDNA, and preferably linkers will attach to both ends of the fragment. In specific embodiments, the linker oligonucleotides will adhere to the cut end of the DNA fragment via ligation or attachment.

In an embodiment of the present invention, a linker-ligated fragment is anchored. In a specific embodiment, the means of anchoring is via an anchorable moiety incorporated into one of the linkers. The means of anchoring may comprise either a covalent or non-covalent interaction. A skilled artisan recognizes the anchorable moiety could be at or near the 5' or 3' end of the linker.

In specific embodiments, the anchorable moiety is a ligand. Examples include biotin or an antibody. Where the anchorable moiety comprises a ligand, it is envisioned that this ligand is the means through which the DNA is immobilized to a substrate. Where the ligand is biotin, the biotin may be attached to streptavidin.

In another embodiment of the invention, it is envisioned that the amplification of the fragment is initiated at primers of a sequence complementary to the first and second linkers respectively. It is further envisioned that this amplification reaction may include: a first amplification primer in which the 5' sequence of the primer is complementary to the first linker sequence and the 3' sequence comprises a specificity region; a second amplification primer, wherein the 5' sequence of said primer is complementary to said second linker sequence and the 3, sequence comprises a specificity region. This method may be further modified to consist of an array of combinations of alternate amplification primers such that the specificity region facilitates the amplification of a substantial percentage of the different sequence templates within a sample. Such an array may be simplified by carrying it out in a multi-well plate.

Amplification of the samples may be further enhanced by pre-amplification with primer pairs complementary to the first and second linker sequences, respectively, prior to amplification with said amplification primers. Further, a partial nucleotide sequence identification of the amplified products may be facilitated by the sequence of the primers used for the amplification. It is envisioned that such identification may be carried out with the aid of a computer program. It is further envisioned that the identification of the amplified DNA may be based on length.

It is envisioned that the 3, specificity region of the first and second primers may be 3 nucleotides long. It is further envisioned that such 3' regions may be either 4, 5, 6, 7 or even 8 base pairs long.

Amplification of the fragments may occur through either the polymerase chain reaction, nucleic acid sequence based amplification, transcription mediated amplification, strand displacement amplification, ligase chain reaction or any other method recognized by a person of ordinary skill in the art to be useful in the amplification of nucleic acid.

It is envisioned that the one or both of the restriction enzymes used to digest the immobilized DNA molecule have either a four, five, six, seven or eight base recognition site. In a preferred embodiment of the invention, the one or both of the restriction enzymes will have a four base pair recognition site. It is envisioned that such restriction enzymes might include but is not limited to: NlaIII, DpnII, Sau3AI, Hsp92II, MboI, NdeII, Bsp143I, Tsp509 I, HhaI, HinP1I, HpaII, MspI, TaqalphaI, MaeII or K2091.

In an additional embodiment of the invention, the amplified product will incorporate a means of detection such that the amplification may be detected and quantified. In a preferred embodiment the means of detection will be a label incorporated into one of the primers used to amplify the fragment or alternatively as a labeled nucleotide incorporated during amplification. It is envisioned that the label may be used to partially identify the sequence information of the amplified product.

It is envisioned that this label could include a chromophore, a fluorophore, an affinity label or a dye. In a further embodiment of the invention a primer would contain an amino moiety and to which a fluorophore could be covalently attached by the reaction of a succinimido ester of the fluorophore to the 5' amino-modified primer. In this embodiment, the fluorophore could include but is not limited to: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

In another additional embodiment, the means of detection may be a nucleotide label incorporated into the product during amplification. It is envisioned that the label attached to the nucleotide could be biotin, DIG, AP, HRP, a fluorescent compound as mentioned in the paragraph above, DNP, or AMCA, to which any of these labels could be attached to after amplification.

While the products of amplification may be labeled for analysis, it is envisioned that other means of analysis may also be employed. The amplification products may be analyzed by polyacrylamide gel electrophoresis, capillary gel electrophoresis, mass spectrophotometry, energy transfer, real-time PCR™, or the Biostar or Luminex technologies.

Analysis may occur to quantify the products. Such quantification may be facilitated by measuring the ratio of each amplified product to a co-amplified reference-gene, or by measuring the ratio of each amplified product to a panel of co-amplified reference-genes.

Analysis of the amplification products may be performed in a multi-well plate, on a gel, on a membrane, or on a solid matrix. Where the analysis takes place on a solid substrate, it is envisioned that the solid substrate may be a DNA chip.

In a preferred embodiment of the invention, the method will be used to compare DNA in a normal cell to DNA in a different cell or tissue, or alternatively to an altered, modified or treated cell. It is envisioned that such alterations, modifications or treatments could include a cell or tissue treated with a pharmaceutical compound, a cell or tissue treated with a teratogenic compound, a cell or tissue treated with a carcinogenic compound, a cell or tissue treated with a toxic compound, a cell or tissue treated with a biological response modifier, a cell or tissue treated with a hormone, a hormone agonist or a hormone antagonist, a cell or tissue treated with a cytokine, a cell or tissue treated with a growth factor, a cell or tissue treated with the ligand of a known biological receptor, a cell or tissue type obtained from different species, a cell or tissue at different stages of development, or a cell or tissue cultured in vitro under different conditions.

It is further envisioned that the method could be used to compare a cell or tissue from two organisms of the same species. Such organisms could further have a known genetic difference. The method may also be used to compare gene expression in a normal cell with gene expression in a diseased cell. It is envisioned that such diseases could include diseases that are infectious, metabolic, genetic, congenital, adaptational, constitutional, drug-related or hereditary.

In an additional embodiment of the invention, the means necessary for performing the method of this invention are included in a kit for detection of gene expression. In a preferred embodiment, such a kit would consist essentially of a first restriction enzyme, a second restriction enzyme, a first, ligatable oligonucleotide tag, a second, ligatable oligonucleotide tag, a third, ligatable labeled-oligonucleotide tag, a fourth, ligatable labeled oligonucleotide tag, a first amplification primer, wherein the 5' sequence of said primer is complementary to said first linker sequence and the 3' sequence comprises a specificity region, a second amplification primer, wherein the 5' sequence of said primer is complementary to said second linker sequence and the 3' sequence comprises a specificity region, and software capable of analyzing data generated from use of the kit. It is envisioned that the kit may contain as the first primer, a primer including the sequence GCTGTCTAGACG (SEQ ID NO:1). It is further envisioned that the kit may contain as the second primer a primer including the sequence CGGTGATGCATC (SEQ ID NO:2). The kit may also include restriction enzymes of a type as previously described. It is envisioned that, as the invention can be adapted to high throughput isolation of RAGEtag fragment libraries, kits could be specifically designed to facilitate such protocols.

It is contemplated that the method described herein and suitable modifications thereof will be used for determining global changes in gene expression patterns in a cell or tissue at any selected time. Appropriate examples include: changes in gene expression patterns due to developmental changes; changes in gene expression patterns due to cancerous transformation in cells; changes in gene expression patterns due to treatment of the cell or organism with a pharmaceutical compound; changes in gene expression patterns due to treatment of the cell or organism with a carcinogen. It is also contemplated that the method will be used for determining gene expression of a transcriptome at any selected time, for new gene discovery, and for diagnostic and/or prognostic purposes.

Thus, in accordance with the present disclosure, the method of the present invention comprises a) obtaining a DNA; b) cleaving the DNA with a first restriction endonuclease; c) cleaving the DNA with a second restriction endonuclease, wherein the cleaving results in releasing a fragment having two nonidentical ends from the DNA; d) ligating a first labeled linker to a first end of the fragment; and e) ligating a second linker to a second end of the fragment, wherein the linkage of both linkers to the fragment produces a linker-ligated fragment. In a specific embodiment, the method further comprises the step of obtaining the linker-ligated fragment by the label. In another specific embodiment, the DNA is immobilized. In a further specific embodiment, step b) further comprises removal of fragments cleaved from the immobilized DNA. In an additional specific embodiment, the obtaining step is further defined as isolating the linker-ligated fragment. In another specific embodiment, isolating the linker-ligated fragment is defined as binding the labeled linker-ligated fragment to a bead. In a further specific embodiment, the binding of the linker-ligated fragment to the bead is through the label. In another specific embodiment, the label is biotin and wherein the bead is coated with streptavidin. In a particular specific embodiment, DNA is immobilized on a magnetic bead. In another specific embodiment, the DNA is immobilized on a magnetic bead through a biotin label, wherein the bead further comprises a coating of streptavidin. In a particular specific embodiment, the ligating steps occur concomitantly.

In a specific embodiment, the method further comprises amplification of the linker-ligated fragment. In a specific embodiment, the amplification is by polymerase chain reaction with two different primers. In another specific embodiment, the DNA is non-genomic DNA. In a further specific embodiment, the DNA is cDNA. In an additional specific embodiment, the immobilizing step further comprises a means of adhering. In another specific embodiment, the means of adhering comprises a means of establishing a non-covalent interaction. In another specific embodiment, the means of adhering comprises a means of establishing a covalent interaction. In a further specific embodiment, the means of adhering comprises a ligand. In an additional specific embodiment, the means of adhering is biotin. In an additional specific embodiment, the means of adhering comprises an antibody. In a specific embodiment, the DNA is immobilized at the 3' end. In a further specific embodiment, the cDNA is reverse transcribed from messenger RNA. In a particular specific embodiment, the reverse transcription is initiated at an oligo dT. In another specific embodiment, the reverse transcription is initiated at a random hexamer. In an additional specific embodiment, the oligo dT is biotinylated. In another specific embodiment, the cDNA is immobilized on a substrate by means of the biotinylated oligo dT. In a specific embodiment, the substrate is streptavidin. In a specific embodiment, the order of the first and the second restriction endonuclease is reversed. In an additional specific embodiment, the amplification is initiated at primers comprising a sequence complementary to the first and the second linkers respectively.

In a further specific embodiment, the amplification is carried out with a primer set comprising a) a first amplification primer, wherein the 5' sequence of the primer is complementary to the first linker sequence and the 3' sequence comprises a specificity region; b) a second amplification primer, wherein the 5' sequence of the primer is complementary to the second linker sequence and the 3' sequence comprises a specificity region. In a specific embodiment, the DNA fragment is preamplified. In a further specific embodiment, the amplification is performed with an array of combinations of alternate amplification primers. In an additional specific embodiment, the method further comprises identifying the amplified DNA. In a specific embodiment, the identification is based upon length. In another specific embodiment, the identification is performed by a computer program. In a further specific embodiment, the amplification is performed in a multi-well plate. In another specific embodiment, the specificity region of the first amplification primer is 3, 4, 5, 6, 7 or 8 base pairs long. In an additional specific embodiment, the specificity region of the second amplification primer is 3, 4, 5, 6, 7 or 8 base pairs long. In an additional specific embodiment, the amplification comprises polymerase chain reaction, nucleic acid sequence based amplification, transcription mediated amplification, strand displacement amplification or ligase chain reaction. In a further specific embodiment, the first restriction endonuclease has a four base pair recognition site. In another specific embodiment, the first restriction endonuclease has a recognition site of five, six, seven or eight base pairs. In a further specific embodiment, the first restriction endonuclease is NlaIII, DpnII, Sau3AI Hsp92II, MboI, NdeII, Bsp143I, Tsp509 I, HhaI, HinP1I, HpaII, MspI, Taqalphal, MaeII or K2091. In a specific embodiment, the second restriction endonuclease has a four base pair recognition site. In another specific embodiment, the second restriction endonuclease has a recognition site of five, six, seven or eight base pairs. In a further specific embodiment, the restriction endonuclease is NlaIII, DpnII, Sau3AI, Hsp92II, MboI, NdeII, Bsp1431, Tsp509 I, HhaI, HinP1I, HpaII, MspI, TaqalphaI, MaeII or K2091. In a specific embodiment, a label is incorporated into the amplified DNA. In a further specific embodiment, the label is incorporated by means of a labeled primer.

In a specific embodiment of the present invention, the method further comprises partial nucleotide sequence identification of the amplified products by the identity of the label. In a specific embodiment, the label is a chromophore, a fluorophore, an affinity label, and/or a dye. In a specific embodiment, the 5, end of the primer comprises an amino moiety and a fluorophore is covalently attached by the reaction of a succinimido ester of the fluorophore to the 5' amino-modified primer. In a specific embodiment, the fluorophore is Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, or Texas Red. In another specific embodiment, the products of the amplification are analyzed. In a specific embodiment, the analysis of amplification products is by polyacrylamide gel electrophoresis, by capillary gel electrophoresis, by mass spectrophotometry, by energy transfer, and/or by OIA technology.

In a specific embodiment, the analysis of amplification products utilizes fluorescently-labeled latex beads. In another specific embodiment, the analysis of amplification products comprises quantifying amplification products. In a further specific embodiment, the quantifying is by measuring the ratio of each amplified product to a co-amplified reference-gene. In another specific embodiment, the quantifying is by measuring the ratio of each amplified product to a panel of co-amplified reference-genes. In an additional specific embodiment, the analysis of amplification products is by real-time PCR. In a specific embodiment, the analysis of amplification products is performed in a multi-well plate. In a specific embodiment, the analysis of amplification products is performed on a membrane. In an additional specific embodiment, the analysis of amplification products is performed on a solid matrix. In a further specific embodiment, the solid matrix is a DNA chip.

In a specific embodiment of the present invention, the method is performed on DNA derived from a normal cell or tissue and on DNA derived from a different cell or tissue. In a specific embodiment, the method is performed on DNA derived from a normal cell or tissue and on DNA derived from a cancerous cell or tissue. In another specific embodiment, the method is performed on DNA derived from a normal cell or tissue and on DNA derived a cell or tissue treated with a pharmaceutical compound. In an additional specific embodiment, the method is performed on DNA derived from a normal cell or tissue and on DNA derived from a cell or tissue treated with a teratogenic compound. In another specific embodiment, the method is performed on DNA derived from a normal cell or tissue and on DNA derived from a cell or tissue treated with a carcinogenic compound. In an additional specific embodiment, the method is performed on DNA derived from a normal cell or tissue and on DNA derived from a cell or tissue treated with a toxic compound. In another specific embodiment, the method is performed on DNA derived from a normal cell or tissue and on DNA derived from a cell or tissue treated with a biological response modifier. In an additional specific embodiment, the method is performed on DNA derived from a normal cell or tissue and on DNA derived from a cell or tissue treated with a hormone, a hormone agonist or a hormone antagonist. In a specific embodiment, the method is performed on DNA derived from a normal cell or tissue and on DNA derived from a cell or tissue treated with a cytokine. In an additional specific embodiment, the method is performed on DNA derived from a normal cell or tissue and on DNA derived from a cell or tissue treated with a growth factor. In an additional specific embodiment, the method is performed on DNA derived from a normal cell or tissue and on the DNA derived from a cell or tissue treated with the ligand of a known biological receptor. In an additional specific embodiment, the method is performed on DNA derived from a cell or tissue type obtained from a different species. In another specific embodiment, the method is performed on DNA derived from a cell or tissue type obtained from a different organism. In an additional specific embodiment, the method is performed on DNA derived from a cell or tissue at different stages of development. In an additional specific embodiment, the method is performed on DNA derived from a normal cell or tissue and on the DNA derived from a cell or tissue that is diseased. In a further specific embodiment, the method is performed on DNA derived from a cell or tissue cultured in vitro under different conditions. In another specific embodiment, the method is performed on the DNA derived from a cell or tissue from two organisms of the same species with a known genetic difference.

In an embodiment of the present invention, there is a kit for detection of gene expression comprising a) a first restriction enzyme; b) a second restriction enzyme; c) a first, ligatable, labeled oligonucleotide tag; d) a second, ligatable, oligonucleotide tag; e) a first amplification primer, wherein the 5' sequence of the primer is complementary to the first oligonucleotide tag and the 3' sequence comprises a specificity region; f) a second amplification primer, wherein the 5' sequence of the primer is complementary to the second oligonucleotide tag and the 3' sequence comprises a specificity region; and g) software capable of analyzing data generated from the kit. In a specific embodiment, the first restriction enzyme is a four base pair cutter. In an additional specific embodiment, the first restriction endonuclease is NlaIII, DpnII, Sau3AI, Hsp92III, MboI, NdeII, Bsp1431, Tsp509 I, HhaI, HinP1I, HpaII, MspI, Taqalphal, MaeII or K2091. In an additional specific embodiment, the second restriction enzyme is a four base pair cutter. In another specific embodiment, the second restriction endonuclease is NlaII, DpnII, Sau3AI, Hsp92II, MboI, NdeII, Bsp1431, Tsp509 I, HhaI, HinP1I, HpaII, MspI, TaqalphaI, MaeII or K2091. In a specific embodiment, the first amplification primer comprises the sequence GCTGTCTAGACG (SEQ ID NO: 1). In another specific embodiment, the second amplification primer comprises the sequence CGGTGATGCATC (SEQ ID NO:2).

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 2A is a schematic of a RAGEtag. FIG. 2B is a B/B restriction fragment. FIG. 2C is a PCR primer alignment on a RAGEtag. The RAGEtags utilize one A and one B primer. FIG. 2D shows a PCR primer alignment on a B/B fragment. The B primer is all that is necessary to amplify this restriction fragment.

FIG. 4A illustrates the protocol of the related art. The restriction fragments comprising linkers from the '600 patent were purified as described therein. PCR was carried out in the presence of only the A primer (lanes 1, 3, 5, 7, 9) or in the presence of both A and B primers (lanes 2, 4, 6, 8, 10). In some cases PCR products can be seen in reactions carried out only in the presence of A primers (lanes 7 and 9). FIG. 4B illustrates the methods described herein, wherein the restriction fragments comprise nonidentical ends. RAGEtags were purified using methods described herein. PCR was carried out in the presence of only the A primer (lanes 2, 4, 6, 8, 10) or in the presence of both A and B primers (lanes 3, 5, 7, 9, 11).

DETAILED DESCRIPTION OF THE PREFERRED EMBODIMENTS

I. Definitions

Figure 1:
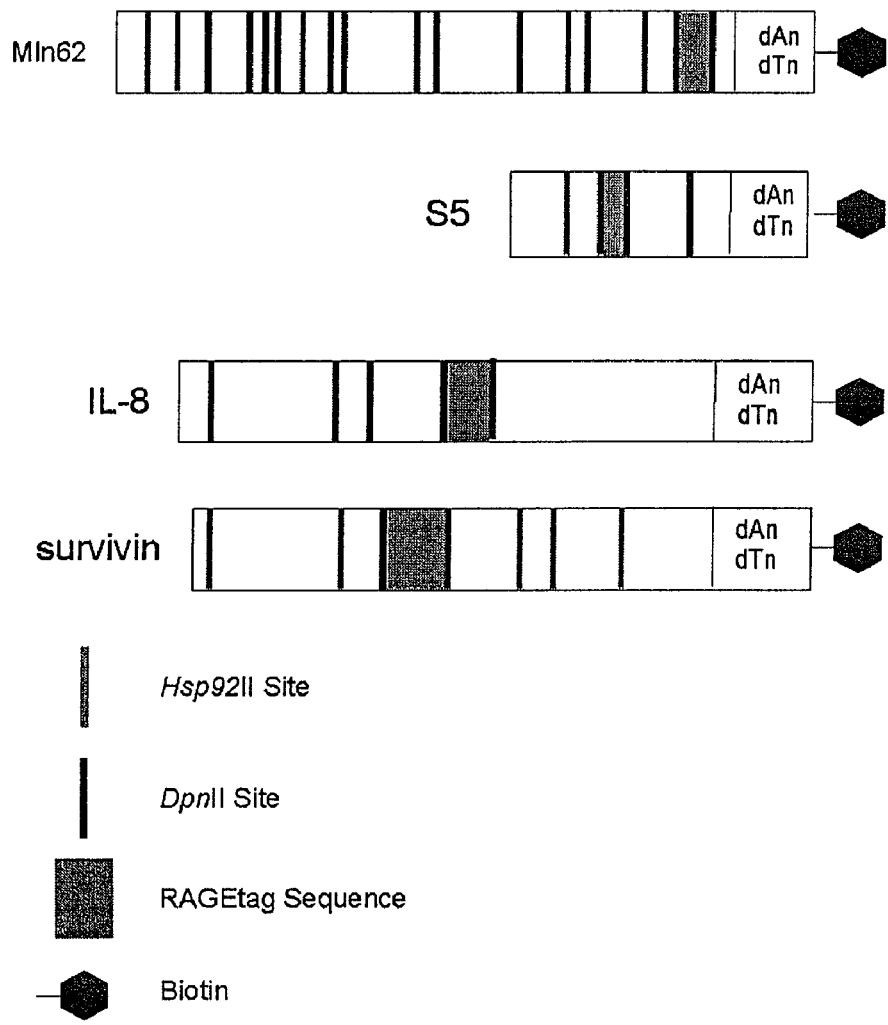
FIG. 1 provides an example illustration showing four representative genes of differing sizes and restriction patterns. The representative genes are Mln62, S5, IL-8 and survivin (top to bottom). Hsp92II restriction sites (A enzyme) are indicated by a narrow light gray rectangle. DpnII sites (B enzyme) are depicted by a black narrow rectangle. The Mln62 and S5 can be analyzed using an "A/B orientation" RAGEtag fragment library, which refers to the order of the restriction digests. Approximately ½ of genes can be analyzed using an A/B RAGEtag fragment library, whereas it is necessary to reverse the order of the digestion enzymes and generate B/A RAGEtag fragment libraries to analyze the other ½ of a genome. IL-8 and survivin represent genes that may be analyzed from B/A orientation RAGEtag fragment libraries. The resulting RAGEtag fragment that will be isolated from the cDNA is indicated by the thick gray rectangle. The 3' end of the genes is shown containing the poly dAn/dTn sequence. In the first step of making a RAGEtag, cDNA is synthesized using a biotinylated oligo dT. The biotin group acts as an anchor to facilitate purification of the desired RAGEtag fragment.

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "anchorable moiety" as used herein refers to a means of adherence or alternatively a means of immobilization.

The term "immobilized" as used herein encompasses a meaning including appended, attached, covalently or non-covalently bound, adhered, ligated, affixed, joined or fused. It is envisioned that the immobilizing may comprise an interaction between the DNA molecule and a substrate that may be either permanent or transitory.

The term "isolating," or "isolated," as used herein regards discriminating a particular DNA fragment from another, such as distinguishing a DNA fragment having nonidentical ends from a DNA fragment having identical ends. Thus, although the term isolated does not necessarily refer to a physical separation of one fragment from another, in some embodiments it may. In specific embodiments, the fragment having nonidentical ends is distinguished from a fragment having identical ends by separating the fragment having nonidentical ends, such as through a differentiating moiety imparted onto the fragment having nonidentical ends, from a fragment having identical ends. In further specific embodiments, the fragment having nonidentical ends is isolated by a label employed on a linker attached to the fragment. In some embodiments, the term "isolated" may be used interchangeably with the terms "removed from the presence of", "separated", and/or "segregated".

The term "nonidentical" as used herein refers to the ends of a single DNA double stranded fragment generated by two different restriction enzymes which generate different end sequences upon cleavage.

II. The Present Invention

The present invention describes improved methods that allow rapid, sensitive and quantitative detection of expression patterns of known as well as unknown genes. The invention regards improvements over known methods in the art to detect gene expression by facilitating the recovery of only one unique restriction fragment from each cDNA species in a collection of products. Thus, the fragment comprising two nonidentical ends is isolated from other fragments via a labeled linker, such as a biotinylated linker, that acts as an anchorable moiety. Use of the anchorable moiety on the linker also facilitates higher yields than the previous state of the art due to the high affinity of binding of the anchorable moiety to the anchor. The overall strategy for these methods is described herein.

To ensure that a single, unique fragment is derived from each cDNA, the cDNAs are first immobilized through an attachment of one end of each cDNA to a solid substrate either prior to or after the first restriction enzyme digestion. For the purposes of illustration, this attachment may be through a biotin label incorporated at the 3' end of the cDNA. A substrate with covalently attached streptavidin can be utilized conveniently to immobilize the cDNA through specific, high affinity binding of biotin to streptavidin. In a preferred embodiment of the invention, the use of a biotinylated oligo dT for reverse transcription would also facilitate the isolation of the resulting cDNA molecule. Using biotinylated oligo dT allows for the isolation of labeled cDNA after it has been reverse transcribed from the mRNA after an initial digestion or, alternatively, facilitates the initial isolation of mRNA on biotinylated oligo dT coated streptavidin beads followed by reverse transcription of the immobilized molecules. It is further envisioned that the DNA may be immobilized via its 5' end. In this embodiment, an anchorable moiety may be incorporated on the 5' end of the polynucleotide molecule through TdT incorporation of labeled nucleotides at the 5' terminus of the molecule (Ying, 1999).

In a preferred embodiment two common and frequently cutting restriction enzymes, such as 4-base-cutters, called for illustrating purposes A and B, are used to excise a unique fragment with defined sticky ends from each DNA. Short linker oligonucleotides, for example 12-mers with appropriate sticky ends, are added to each end, creating a fragment library of "RAGEtags." It is an important feature of the present invention that when evaluating gene expression, no single molecular species of cDNA gives rise to more than one fragment in the collection of "RAGEtags."

The use of 4-base cutter restriction enzymes in the preparation of RAGEtag fragment libraries permits the analysis of virtually any DNA molecule since recognition sites for both the enzymes will be present in virtually any DNA. However, only about half of the DNAs will have a B recognition site closer to the 3' end than any A recognition site. Thus, after the first (A) restriction cut, only about half of the retained DNAs will contain a B restriction recognition sequence, and thus produce a fragment in the A/B RAGEtags. The remaining half of the DNAs will have an A recognition site closer to the 3' end than any B recognition site. In a preferred embodiment the order in which the A and B cuts are made is reversed, allowing appropriate fragments to be obtained from the other portion of the genome. After addition of linkers these fragments are designated "B/A RAGEtags." The combination of B/A and A/B RAGEtag fragment libraries would therefore encompass virtually all of the expressed genes present in a given sample.

In a preferred embodiment for generation of an A/B orientation RAGEtag fragment library, immobilized cDNA is cleaved with a restriction endonuclease, such as Hsp92II (A), leaving a 4-base overhang upon digestion. All Hsp92II fragments except the 3' terminal fragment are released from the magnetic bead and discarded. The immobilized library of fragments are digested with a second 4-base overhang creating restriction enzyme, such as DpnII (B), releasing the fragments from the anchor. The released cDNA is precipitated using carboxylated magnetic beads. A biotinylated A linker and unmodified B linker are then ligated to the digested ends of the released fragments. The ligated fragments are recovered using streptavidin magnetic beads. Any fragments containing two ends comprised from DpnII are discarded.

For generation of a B/A orientation RAGEtag fragment library, the immobilized cDNA is cleaved with the restriction endonuclease DpnII, leaving a 4-base overhang upon digestion. All DpnII fragments except the 3' terminal fragment are released from the magnetic bead and discarded. The immobilized fragments containing DpnII ends are digested with a second 4-base overhang creating restriction enzyme, Hsp92II, releasing the fragments from the anchor. The released fragments are precipitated using ethanol, glycogen and carboxylated magnetic beads. A biotinylated B linker and unmodified A linker are then ligated to the digested ends of the released fragments. The ligated fragments are recovered using streptavidin magnetic beads. Any fragments containing two ends comprised from Hsp92II are discarded.

In further specific embodiments, the released fragments are precipitated onto carboxylate-modified encapsulated magnetic beads using ethanol, such as absolute ethanol, and substantially no salt. In specific embodiments, the solutions substantially lack a chaotropic agent or polyalkylene glycol. The carboxylate-modified beads (about 50 mg/mL) are washed with ethanol, preferably thrice, resuspended in an ethanol solution, and placed on ice. In specific embodiments, the nucleic acid solution contains glycogen is combined with the washed beads and incubated on ice for about 15 mins. In a specific embodiment, the glycogen concentration is about 20 mg/mL to about 120 mg/mL, preferably about 60 mg/mL.

The bead/nucleic acid slurry is placed next to a magnet, and the supernatant is discarded. In specific embodiments, the precipitated material on the beads is washed, preferably thrice, with a 70% ethanol solution that removes impurities. Nucleic acids are then recovered by solubilization in a standard solution such as water or 10 mM Tris, 1 mM EDTA, pH 8.0 (TE).

These RAGEtag fragment libraries are then used as template for PCR reactions with a combinatorial library of primers. A combinatorial library of 320 primers is used to selectively amplify any genes of choice using the RAGEtag fragment library as the template. The PCR primers for are designed to provide specificity and uniform conditions in the PCR reactions. There are two sets of primers. Each set contains a common region derived from the linker. The 3' end of each primer comprises a specificity region of 3 to 4 nucleotides. The specificity region facilitates the amplification of a small number of different genes in a sample. There are a total of 256 A primers with 4-base specificity and 64 B primers with 3-base specificity. These primers may be combined pairwise with the two orientations of RAGEtag to produce (256×64×2=) 32,768 unique reactions. The presence of a relatively long common region (16 basepairs) in the RAGE primers allows optimal amplification with all primers under a single set of PCR conditions. PCR is performed at a single set of reaction conditions using a thermostable polymerase. The conditions are such that the amount of product generated is proportional to the concentration of the template (RAGEtag) added to the reaction.

A skilled artisan recognizes that linkers added to the ends of the fragments may comprise any sequence which indirectly or directly facilitates segregation, removal, isolation, and so forth of a fragment having two non-identical ends from a fragment having two identical ends. In addition, the linker sequence may comprise any sequence which facilitates amplification of the fragment either by indirect or direct means. In a specific embodiment, the fragment having two non-identical ends is ligated with a linker having sequence which comprises PCR™ primer binding sites for amplification of the fragment by PCR™.

In a specific embodiment of the present invention, the following sequences for the linkers are utilized: A-linker 5'-CGTCTAGACAGC (previously phosphorylated with T4 polynucleotide kinase) (SEQ ID NO:3); and 5'-GCTGTCTAGACGCATG (SEQ ID NO:4) and; B-linker 5'-CGGTGATGCATC (SEQ ID NO:5) and 5'-GATCGATGCATCACCG (previously phosphorylated with T4 polynucleotide kinase) (SEQ ID NO:6). In further specific embodiments, two sets of primers for PCR™ reactions are utilized, corresponding to the A- and B-linkers above, but containing 3 or 4 nucleotide specificity regions at the 3' end. Sequences of these primer sets comprise: A-end (256 primers)-5'-GCGTCTAGACGCATGNNNN (SEQ ID NO:7); and B-end (64 primers)-5'-CGGTGATGCATCGATCNNN (SEQ ID NO:8).

A preferred embodiment of the invention comprises the ability to detect changes in the pattern of gene expression, for example, in the same cell type in different developmental stages, under different physiologic or pathologic conditions, when treated with different pharmaceuticals, mutagens, carcinogens, etc. allows the identification of genes as candidates for gene based therapies. It is however envisioned that the methods of the present invention may be utilized to analyze cellular DNA, genomic DNA, mitochondrial DNA, cDNA and synthetic DNA.

For known cDNAs, such as are present in the National Center for Biotechnology Information's Genbank database, the pair of primers that will amplify the gene-specific target can be predicted from the sequence, as well as the size of the resulting amplimer. The intensity of the amplified product band on a polyacrylamide gel is the relative measure of the frequency of the corresponding mRNA in the total population of mRNAs. The primers may also be labeled with a tag or dye. In this case the amplified product could be analyzed via capillary electrophoresis.

To obtain a unique specification, further information can be obtained by size fractionation of the amplimer products or by testing for the presence of other restriction enzyme recognition sequences or by determining the sequence of the amplimer. Changes in the length of the two specificity regions, in an alternative embodiment, will alter the total number of unique reactions that must be performed to assay the entire genome. If n is the sum of the lengths of the two specificity regions, the number of unique reactions is $2\times4^N$.

In principle, relative measurements of the expression of all genes in the genome can be obtained with the method described above by carrying out all 32,768 unique reactions and measuring the amount of each amplimer formed. In practice, it often is desirable to measure the expression levels for a particular subset of known genes, for example, all known genes that code for cyclins. To do this, prior knowledge of the sequence of each mRNA is needed in order to predict the exact sequences of the primers to be used for its amplification, and to predict the length, or other identifying properties, of the corresponding amplimer.

Computer code that can be executed on a digital computer has been written and used to construct a database for this purpose. One method implementing such a program involves importing clustering information from publicly available databases of the National Library of Medicine, importing mRNA sequence information from publicly available databases of the National Library of Medicine. The necessary information is then extracted and manipulated and the data from the different databases integrated (primer locations and sequences, polyA signals, coding sequences, LocusLink and Unigene numbers, etc.). The information is then stored in a local database and a user interface provided for data display and searches. With the benefit of the present disclosure, those having skill in the art will recognize that other methods for forming a computer program with the disclosed function are available.

All mRNA sequences existing in the publicly available GenBank database that are derived from all eukaryotic organisms have been separately loaded into this database, and the positions, sequences, orientations and lengths of the corresponding RAGEtags that would be obtained with two particular restriction enzymes, Hsp92II and DpnII, have been extracted from the sequence information, as well as the sequences of the A-end and B-end primers needed to amplify these RAGEtags. In addition, computer code has been written and used to update the database each month, adding information from sequences that have recently been deposited in GenBank. Additionally, computer code has been written that allows individual GenBank files to be searched for the above information, and also that allows GenBank libraries to be searched for entries that would be amplified by a given pair of A-end and B-end primers.

U.S. Pat. No. 6,221,600 is incorporated by reference herein in its entirety for background purposes, with respect to the present invention.

III. Nucleic Acids

Genes are sequences of DNA in an organism's genome encoding information that is converted into various products making up a whole cell. They are expressed by the process of transcription, which involves copying the sequence of DNA into RNA. Most genes encode information to make proteins, but some encode RNAs involved in other processes. If a gene encodes a protein, its transcription product is called mRNA ("messenger" RNA). After transcription in the nucleus (where DNA is located), the mRNA must be transported into the cytoplasm for the process of translation, which converts the code of the mRNA into a sequence of amino acids to form protein. In order to direct transport into the cytoplasm, the 3' ends of mRNA molecules are post-transcriptionally modified by addition of several adenylate residues to form the "polyA" tail. This characteristic modification distinguishes gene expression products destined to make protein from other molecules in the cell, and thereby provides one means for detecting and monitoring the gene expression activities of a cell.

Some of the exemplary genes that may be monitored for expression are genes involved in cancer pathways, for example, oncogenes, tumor suppressor genes, DNA repair genes, genes involved in signal transduction, etc. Loss of control of cell-cycle regulatory genes, or genes controlling apoptotic pathways can lead to the development of cancers.

Other genes that may be monitored for changes in expression levels are genes that change in response to a pharmaceutical compound, or genes that are involved in metabolism and disposition of pharmaceutical compounds, hormones or toxicants. This can pinpoint genes involved in pathways of the pathological condition.

Yet other genes that can be monitored are genes that change in response to development and growth, or those are responsible for controlling developmental pathways. Studies directed towards aging for example can benefit vastly from these type of experiments.

Furthermore, gene expression changes may be monitored in response to treatment of cells or tissues with a host of chemical compounds such as mutagens, teratogens, carcinogens, pesticides, pollutants, etc., or biological compounds such as hormones, growth factors, cytokines, etc.

Patterns of expression for genes not connected with the pathways mentioned previously, as well as genes whose function is not yet identified, can be monitored for the purpose of establishing expression patterns that may be of diagnostic or prognostic values, or may be indicative of past or current exposure to certain pharmaceutical compounds, toxicants or drugs of abuse.

IV. Detection of Nucleic Acids

A. Oligonucleotide Probes and Primers

Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of annealing to the nucleic acid segment being described under relatively stringent conditions such as those described herein.

Primers should be of sufficient length to provide specific annealing to an RNA or DNA tissue sample. The use of a primer of between about 10–14, 15–20, 21–30 or 31–40 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained.

Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 300, 500, 600, 700, 800, and longer are contemplated as well. Accordingly, nucleotide sequences may be selected for their ability to selectively form duplex molecules with complementary stretches of genes or RNAs or to provide primers for amplification of DNA or RNA from cells, cell lysates and tissues. The method of using probes and primers of the present invention is in the selective amplification and detection of genes, changes in gene expression, gene polymorphisms, single nucleotide polymorphisms, changes in mRNA expression wherein one could be detecting virtually any gene or genes of interest from any species. The target polynucleotide will be RNA molecules, mRNA, cDNA, DNA or amplified DNA. By varying the stringency of annealing, and the region of the primer, different degrees of homology may be discovered.

The particular amplification primers of the present invention will be specific oligonucleotides which encode particular features including the recognition site for frequently cutting restriction enzymes, primer sequences, and degenerate sequences of 3, 4, 5, 6, 7, 8 or more consecutive bases to ensure amplification of all target genes. Generally, the present invention may involve the use of a variety of other PCR.™. primers which hybridize to a variety of other target sequences.

Amplification primers may be chemically synthesized by methods well known within the art (Agrawal, 1993). Chemical synthesis methods allow for the placement of detectable labels such as fluorescent labels, radioactive labels etc. to be placed virtually anywhere within the polynucleic acid sequence. Solid phase method of synthesis also may be used.

The amplification primers may be attached to a solid-phase, for example, a latex bead; or the surface of a chip. Thus, the amplification carried out using these primers will be on a solid support/surface.

Furthermore, some primers of the present invention will have a recognition moiety attached. A wide variety of appropriate recognition means are known in the art, including fluorescent labels, radioactive labels, mass labels, affinity labels, chromophores, dyes, electroluminescence, chemiluminescence, enzymatic tags, or other ligands, such as avidin/biotin, or antibodies, which are capable of being detected and are described below.

B. Amplification

1. PCR™

In some embodiments, poly-A mRNA is isolated and reverse transcribed (referred to as RT) to obtain cDNA which is then used as a template for polymerase chain reaction (referred to as PCRT™) based amplification. In other embodiments, cDNA may be obtained and used as a template for the PCR™ reaction. In PCR™, pairs of primers that selectively hybridize to nucleic acids are used under conditions that permit selective hybridization. The term primer, as used herein, encompasses any nucleic acid that is capable of priming the synthesis of a nascent nucleic acid in a template-dependent process. Primers may be provided in double-stranded or single-stranded form, although the single-stranded form is preferred.

The primers are used in any one of a number of template dependent processes to amplify the target-gene sequences present in a given template sample. One of the best known amplification methods is PCR™ which is described in detail in U.S. Pat. Nos. 4,683,195, 4,683,202 and 4,800,159, each incorporated herein by reference.

In PCR™, two primer sequences are prepared which are complementary to regions on opposite complementary strands of the target-gene(s) sequence. The primers will hybridize to form a nucleic-acid:primer complex if the target-gene(s) sequence is present in a sample. An excess of deoxyribonucleoside triphosphates is added to a reaction mixture along with a DNA polymerase, e.g., Taq polymerase, that facilitates template-dependent nucleic acid synthesis.

If the target-gene(s) sequence:primer complex has been formed, the polymerase will cause the primers to be extended along the target-gene(s) sequence by adding on nucleotides. By raising and lowering the temperature of the reaction mixture, the extended primers will dissociate from the target-gene(s) to form reaction products, excess primers will bind to the target-gene(s) and to the reaction products and the process is repeated. These multiple rounds of amplification, referred to as "cycles", are conducted until a sufficient amount of amplification product is produced.

Next, the amplification product is detected. In certain applications, the detection may be performed by visual means. Alternatively, the detection may involve indirect identification of the product via fluorescent labels, chemiluminescence, radioactive scintigraphy of incorporated radiolabel or incorporation of labeled nucleotides, mass labels or even via a system using electrical or thermal impulse signals (Affymax technology).

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641, filed Dec. 21, 1990.

2. LCR

Another method for amplification is the ligase chain reaction ("LCR"), disclosed in European Patent No. 320, 308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

3. Qbeta Replicase

Qbeta Replicase, described in WO 87/06270, also may be used as still another amplification method in the present invention. In this method, a replicative sequence of RNA which has a region complementary to that of a target is added to a sample in the presence of an RNA polymerase. The polymerase will copy the replicative sequence which can then be detected.

4. Isothermal Amplification

An isothermal amplification method, in which restriction endonucleases and ligases are used to achieve the amplification of target molecules that contain nucleotide 5'-[α-thio]-triphosphates in one stand of a restriction site also may be useful in the amplification of nucleic acids in the present invention. Such an amplification method is described by Walker et al. 1992, incorporated herein by reference.

5. Strand Displacement Amplification

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

6. Cyclic Probe Reaction

Target specific sequences can also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

7. Transcription-Based Amplification

Other nucleic acid amplification procedures include transcription-based amplification systems (rAS), including nucleic acid sequence based amplification (NASBA) and 3SR, Kwoh et al., 1989; PCT Patent Application WO 88/10315 et al., 1989, each incorporated herein by reference).

In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate target specific sequences.

8. Other Amplification Methods

Other amplification methods, as described in British Patent No. GB 2,202,328, and in WO 89/09284, each incorporated herein by reference, may be used in accordance with the present invention. In the former application, "modified" primers are used in a PCR™. like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Davey et al., European Patent No. 329,822 (incorporated herein by reference) disclose a nucleic acid amplification process involving cyclically synthesizing single-stranded RNA ("ssRNA"), ssDNA, and double-stranded DNA (ds-DNA), which may be used in accordance with the present invention.

The ssRNA is a first template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("ds-DNA") molecule, having a sequence identical to that of the original RNA between the primers and having additionally, at one end, a promoter sequence. This promoter sequence can be used by the appropriate RNA polymerase to make many RNA copies of the DNA. These copies can then reenter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Patent Application WO 89/06700 (incorporated herein by reference) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts.

Other suitable amplification methods include "race" and "one-sided PCR™" (Frohman, 1990; Ohara et al., 1989, each herein incorporated by reference). Methods based on ligation of two (or more) oligonucleotides in the presence of nucleic acid having the sequence of the resulting "di-oligonucleotide", thereby amplifying the di-oligonucleotide, also may be used in the amplification step of the present invention, Wu et al., 1989, incorporated herein by reference).

V. Enzymes

A. Restriction Enzymes

Restriction-enzymes recognize specific short DNA sequences four to eight nucleotides long (see Table 1), and cleave the DNA at a site within this sequence. In the context of the present invention, restriction enzymes are used to cleave cDNA molecules at sites corresponding to various restriction-enzyme recognition sites. Frequently cutting enzymes, such as the four-base cutter enzymes, are preferred as this yields DNA fragments that are in the right size range for subsequent amplification reactions. Some of the preferred four-base cutters are NlaIII, DpnII, Sau3AI, Hsp92II, MboI, NdeII, Bsp1431, Tsp509 I, MhaI, HinP1I HpaII, MspI, Taq alphaI, MaeII or K2091.

As the sequence of the recognition site is known (see list below), primers can be designed comprising nucleotides corresponding to the recognition sequences. If the primer sets have in addition to the restriction recognition sequence, degenerate sequences corresponding to different combinations of nucleotide sequences, one can use the primer set to amplify DNA fragments that have been cleaved by the particular restriction enzyme. The list below exemplifies the currently known restriction enzymes that may be used in the invention.

TABLE I

RESTRICTION ENZYMES

| Enzyme Name | Recognition Sequence | |
|---|---|---|
| AatII | GACGTC | |
| Acc65 I | GGTACC | |
| Acc I | GTMKAC | |
| Aci I | CCGC | |
| Acl I | AACGTT | |
| Afe I | AGCGCT | |
| Afl II | CTTAAG | |
| Afl III | ACRYGT | |
| Age I | ACCGGT | |
| Ahd I | GACNNNNNGTC | (SEQ ID NO:9) |
| Alu I | AGCT | |
| Alw I | GGATC | |
| AlwN I | CAGNNNCTG | |
| Apa I | GGGCCC | |
| ApaL I | GTGCAC | |

TABLE I-continued

RESTRICTION ENZYMES

| Enzyme Name | Recognition Sequence | |
|---|---|---|
| Apo I | RAATTY | |
| Asc I | GGCGCGCC | |
| Ase I | ATTAAT | |
| Ava I | CYCGRG | |
| Ava II | GGWCC | |
| Avr II | CCTAGG | |
| Bae I | NACNNNNGTAPyCN | (SEQ ID NO:10) |
| BamH I | GGATCC | |
| Ban I | GGYRCC | |
| Ban II | GRGCYC | |
| Bbs I | GAAGAC | |
| Bbv I | GCAGC | |
| BbvC I | CCTCAGC | |
| Bcg I | CGANNNNNNTGC | (SEQ ID NO:11) |
| BciV I | GTATCC | |
| Bcl I | TGATCA | |
| Bfa I | CTAG | |
| Bgl I | GCCNNNNNGGC | (SEQ ID NO:12) |
| Bgl II | AGATCT | |
| Blp I | GCTNAGC | |
| Bmr I | ACTGGG | |
| Bpm I | CTGGAG | |
| BsaA I | YACGTR | |
| BsaB I | GATNNNNATC | (SEQ ID NO:13) |
| BsaH I | GRCGYC | |
| Bsa I | GGTCTC | |
| BsaJ I | CCNNGG | |
| BsaW I | WCCGGW | |
| BseR I | GAGGAG | |
| Bsg I | GTGCAG | |
| BsiE I | CGRYCG | |
| BsiHKA I | GWGCWC | |
| BsiW I | CGTACG | |
| Bsl I | CCNNNNNNNGG | (SEQ ID NO:14) |
| BsmA I | GTCTC | |
| BsmB I | CGTCTC | |
| BsmF I | GGGAC | |
| Bsm I | GAATGC | |

TABLE I-continued

RESTRICTION ENZYMES

| Enzyme Name | Recognition Sequence | |
|---|---|---|
| BsoB I | CYCGRG | |
| Bsp1286 I | GDGCHC | |
| BspD I | ATCGAT | |
| BspE I | TCCGGA | |
| BspH I | TCATGA | |
| BspM I | ACCTGC | |
| BsrB I | CCGCTC | |
| BsrD I | GCAATG | |
| BsrF I | RCCGGY | |
| BsrG I | TGTACA | |
| Bsr I | ACTGG | |
| BssH II | GCGCGC | |
| BssK I | CCNGG | |
| Bst4C I | ACNGT | |
| BssS I | CACGAG | |
| BstAP I | GCANNNNNTGC | (SEQ ID NO:15) |
| BstB I | TTCGAA | |
| BstE II | GGTNACC | |
| BstF5 I | GGATGNN | |
| BstN I | CCWGG | |
| BstU I | CGCG | |
| BstX I | CCANNNNNNTGG | (SEQ ID NO:16) |
| BstY I | RGATCY | |
| BstZ17 I | GTATAC | |
| Bsu36 I | CCTNAGG | |
| Btg I | CCPuPyGG | |
| Btr I | CACGTG | |
| Cac8 I | GCNNGC | |
| Cla I | ATCGAT | |
| Dde I | CTNAG | |
| Dpn I | GATC | |
| Dpn II | GATC | |
| Dra I | TTTAAA | |
| Dra III | CACNNNGTG | |
| Drd I | GACNNNNNNGTC | (SEQ ID NO:17) |
| Eae I | YGGCCR | |
| Eag I | CGGCCG | |

TABLE I-continued

RESTRICTION ENZYMES

| Enzyme Name | Recognition Sequence | |
|---|---|---|
| Ear I | CTCTTC | |
| Eci I | GGCGGA | |
| EcoN I | CCTNNNNNAGG | (SEQ ID NO:18) |
| EcoO109 I | RGGNCCY | |
| EcoR I | GAATTC | |
| EcoR V | GATATC | |
| Fau I | CCCGCNNNN | |
| Fnu4H I | GCNGC | |
| Fok I | GGATG | |
| Fse I | GGCCGGCC | |
| Fsp I | TGCGCA | |
| Hae II | RGCGCY | |
| Hae III | GGCC | |
| Hga I | GACGC | |
| Hha I | GCGC | |
| Hinc II | GTYRAC | |
| Hind III | AAGCTT | |
| Hinf I | GANTC | |
| HinPl I | GCGC | |
| Hpa I | GTTAAC | |
| Hpa II | CCGG | |
| Hph I | GGTGA | |
| Kas I | GGCGCC | |
| Kpn I | GGTACC | |
| Mbo I | GATC | |
| Mbo II | GAAGA | |
| Mfe I | CAATTG | |
| Mlu I | ACGCGT | |
| Mly I | GAGTCNNNNN | (SEQ ID NO:19) |
| Mnl I | CCTC | |
| Msc I | TGGCCA | |
| Mse I | TTAA | |
| Msl I | CAYNNNNRTG | (SEQ ID NO:20) |
| MspAl I | CMGCKG | |
| Msp I | CCGG | |
| Mwo I | GCNNNNNNNGC | (SEQ ID NO:21) |
| Nae I | GCCGGC | |
| Nar I | GGCGCC | |

TABLE I-continued

RESTRICTION ENZYMES

| Enzyme Name | Recognition Sequence | |
|---|---|---|
| Nci I | CCSGG | |
| Nco I | CCATGG | |
| Nde I | CATATG | |
| NgoMI V | GCCGGC | |
| Nhe I | GCTAGC | |
| Nla III | CATG | |
| Nla IV | GGNNCC | |
| Not I | GCGGCCGC | |
| Nru I | TCGCGA | |
| Nsi I | ATGCAT | |
| Nsp I | RCATGY | |
| Pac I | TTAATTAA | |
| PaeR7 I | CTCGAG | |
| Pci I | ACATGT | |
| PflF I | GACNNNGTC | |
| PflM I | CCANNNNNTGG | (SEQ ID NO:22) |
| PleI | GAGTC | |
| Pme I | GTTTAAAC | |
| Pml I | CACGTG | |
| PpuM I | RGGWCCY | |
| PshA I | GACNNNNGTC | (SEQ ID NO:23) |
| Psi I | TTATAA | |
| PspG I | CCWGG | |
| PspOM I | GGGCCC | |
| Pst I | CTGCAG | |
| Pvu I | CGATCG | |
| Pvu II | CAGCTG | |
| Rsa I | GTAC | |
| Rsr II | CGGWCCG | |
| Sac I | GAGCTC | |
| Sac II | CCGCGG | |
| Sal I | GTCGAC | |
| Sap I | GCTCTTC | |
| Sau3A I | GATC | |
| Sau96 I | GGNCC | |
| Sbf I | CCTGCAGG | |
| Sca I | AGTACT | |

TABLE I-continued

RESTRICTION ENZYMES

| Enzyme Name | Recognition Sequence | |
|---|---|---|
| ScrF I | CCNGG | |
| SexA I | ACCWGGT | |
| SfaN I | GCATC | |
| Sfc I | CTRYAG | |
| Sfi I | GGCCNNNNNGGCC | (SEQ ID NO:24) |
| Sfo I | GGCGCC | |
| SgrA I | CRCCGGYG | |
| Sma I | CCCGGG | |
| Sml I | CTYRAG | |
| SnaB I | TACGTA | |
| Spe I | ACTAGT | |
| Sph I | GCATGC | |
| Ssp I | AATATT | |
| Stu I | AGGCCT | |
| Sty I | CCWWGG | |
| Swa I | ATTTAAAT | |
| Taq I | TCGA | |
| Tfi I | GAWTC | |
| Tli I | CTCGAG | |
| Tse I | GCWGC | |
| Tsp45 I | GTSAC | |
| Tsp509 I | AATT | |
| TspR I | CAGTG | |
| Tth111 I | GACNNNGTC | |
| Xba I | TCTAGA | |
| Xcm I | CCANNNNNNNNNTGG | (SEQ ID NO:25) |
| Xho I | CTCGAG | |
| Xma I | CCCGGG | |
| Xmn I | GAANNNNTTC | (SEQ ID NO:26) |

B. Other Enzymes

Other enzymes that may be used in conjunction with the invention include nucleic acid modifying enzymes listed in the following tables.

TABLE 2

POLYMERASES AND REVERSE TRANSCRIPTASES

Thermostable DNA Polymerases:

OmniBase ™ Sequencing Enzyme
Pfu DNA Polymerase
Taq DNA Polymerase

TABLE 2-continued

POLYMERASES AND REVERSE TRANSCRIPTASES

Taq DNA Polymerase, Sequencing Grade
TaqBead ™ Hot Start Polymerase
AmpliTaq Gold
Tfl DNA Polymerase
Tli DNA Polymerase
Tth DNA Polymerase
DNA Polymerases:

DNA Polymerase I, Klenow Fragment, Exonuclease Minus
DNA Polymerase I
DNA Polymerase I Large (Klenow) Fragment
Terminal Deoxynucleotidyl Transferase
T4 DNA Polymerase
Reverse Transcriptases:

AMV Reverse Transcriptase
M-MLV Reverse Transcriptase

TABLE 3

DNA/RNA MODIFYING ENZYMES

| Ligases: | T4 DNA Ligase |
|---|---|
| Kinases: | T4 Polynucleotide Kinase |

VI. Labels

Recognition moieties incorporated into primers, incorporated into the amplified product during amplification, or attached to probes are useful in identification of the amplified molecules. A number of different labels may be used for the purpose such as fluorophores, chromophores, radioisotopes, enzymatic tags, antibodies, chemniluminescence, electroluminescence, affinity labels, etc. One of skill in the art will recognize that these and other fluorophores not mentioned herein can also be used with success in this invention.

Examples of affinity labels include but are not limited to the following: an antibody, an antibody fragment, a receptor protein, a hormone, biotin, DNP, or any polypeptide/protein molecule that binds to an affinity label and may be used for separation of the amplified gene.

Examples of enzyme tag include enzymes such as such as urease, alkaline phosphatase or peroxidase to mention a few and colorimetric indicator substrates can be employed to provide a detection means visible to the human eye or spectrophotometrically, to identify specific hybridization with complementary nucleic acid-containing samples. All these examples are generally known in the art and the skilled artisan will recognize that the invention is not limited to the examples described above.

The following fluorophores are specifically contemplated to be useful in practicing the present invention. Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

VII. Methods of Immobilization

Immobilization of the DNA may be achieved by a variety of methods involving either non-covalent or covalent interactions between the immobilized DNA comprising an anchorable moiety and an anchor. In a preferred embodiment of the invention immobilization consists of the non-covalent coating of a solid phase with streptavidin or avidin and the subsequent immobilization of a biotinylated polynucleotide (Holmstrom, 1993). It is envisioned that DNA may bind to magnetic beads with surface carboxyl groups (Hawkins, 1994; Denagelis, 1995, Skowronski, 2000). It is further envisioned that immobilization may occur by precoating a polystyrene or glass solid phase with poly-L-Lys or poly L-Lys, Phe, followed by the covalent attachment of either amino- or sulfhydryl-modified polynucleotides using bifunctional crosslinking reagents (Running, 1990 and Newton, 1993).

Immobilization may also take place by the direct covalent attachment of short, 5'-phosphorylated primers to chemically modified polystyrene plates ("Covalink" plates, Nunc) Rasmussen, (1991). The covalent bond between the modified oligonucleotide and the solid phase surface is introduced by condensation with a water-soluble carbodiimide. This method facilitates a predominantly 5'-attachment of the oligonucleotides via their 5'-phosphates.

Nikiforov et al. (U.S. Pat. No. 5,610,287 incorporated herein by reference) describes a method of non-covalently immobilizing nucleic acid molecules in the presence of a salt or cationic detergent on a hydrophilic polystyrene solid support containing a hydrophilic moiety or on a glass solid support. The support is contacted with a solution having a pH of about 6 to about 8 containing the synthetic nucleic acid and a cationic detergent or salt. The support containing the immobilized nucleic acid may be washed with an aqueous solution containing a non-ionic detergent without removing the attached molecules.

Another commercially available method envisioned by the inventors to facilitate immobilization is the "Reacti-Bind™ DNA Coating Solutions" (see "Instructions—Reacti-Bind™ DNA Coating Solution" January 1997). This product comprises a solution that is mixed with DNA and applied to surfaces such as polystyrene or polypropylene. After overnight incubation, the solution is removed, the surface washed with buffer and dried, after which it is ready for hybridization. It is envisioned that similar products, i.e. Costar "DNA-BIND™" (DNA immobilization surface) or Immobilon-AV Affinity Membrane (IAV, Millipore, Bedford, Mass.) are equally applicable to immobilize the respective fragment.

VIII. Separation and Quantitation Methods

Following amplification, it may be desirable to separate the amplification products of several different lengths from each other and from the template and the excess primer for the purpose analysis or more specifically for determining whether specific amplification has occurred.

A. Gel Electrophoresis

In one embodiment, amplification products are separated by agarose, agarose-acrylamide or polyacrylamide gel electrophoresis using standard methods (Sambrook et al., 1989).

B. Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982). In yet another alternative, labeled cDNA products, such as biotin or antigen can be captured with beads bearing avidin or antibody, respectively.

C. Microfluidic Techniques

Microfluidic techniques include separation on a platform such as microcapillaries, designed by ACLARA BioSciences Inc., or the LabChip™"liquid integrated circuits" made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487 and 5,296,375, discuss devices for collection and analysis of cell containing samples and are incorporated herein by reference. U.S. Pat. No. 5,856,174 describes an apparatus which combines the various processing and analytical operations involved in nucleic acid analysis and is incorporated herein by reference.

D. Capillary Electrophoresis

In some embodiments, it may be desirable to provide an additional, or alternative means for analyzing the amplified genes. In these embodiment, micro capillary arrays are contemplated to be used for the analysis.

Microcapillary array electrophoresis generally involves the use of a thin capillary or channel which may or may not be filled with a particular separation medium. Electrophoresis of a sample through the capillary provides a size based separation profile for the sample. The use of microcapillary electrophoresis in size separation of nucleic acids has been reported in, for example, Woolley and Mathies, 1994. Microcapillary array electrophoresis generally provides a rapid method for size-based sequencing, PCR.™. product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, for example, Jacobsen et al., 1994; Effenhauser et al., 1994; Harrison et al., 1993; Effenhauser et al., 1993; Manz et al., 1992; and U.S. Pat. No. 5,904,824, here incorporated by reference. Typically, these methods comprise photolithographic etching of micron scale channels on a silica, silicon or other crystalline substrate or chip, and can be readily adapted for use in the present invention. In some embodiments, the capillary arrays may be fabricated from the same polymeric materials described for the fabrication of the body of the device, using the injection molding techniques described herein.

Tsuda et al., 1990, describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

E. Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods in the known in the art can be found summarized in Methods in Enzymology, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include Schram, 1990 and Crain, 1990 here incorporated by reference. The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al. Biomedical Environmental Mass Spectrometry 14, 111–116 (1987)).

Two ionization/desorption techniques are electrospray/ionspray (ES) and matrix-assisted laser desorption/ionization (MALDI). ES mass spectrometry was introduced by Fenn, 1984; PCT Application No. WO 90/14148 and its applications are summarized in review articles, for example, Smith 1990 and Ardrey, 1992. As a mass analyzer, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp 1990. Since, in most cases, no multiple molecular ion peaks are produced with this technique, the mass spectra, in principle, look simpler compared to ES mass spectrometry. DNA molecules up to a molecular weight of 410,000 daltons could be desorbed and volatilized (Williams, 1989). More recently, this the use of infrared lasers (IR) in this technique (as opposed to UV-lasers) has been shown to provide mass spectra of larger nucleic acids such as, synthetic DNA, restriction enzyme fragments of plasmid DNA, and RNA transcripts up to a size of 2180 nucleotides (Berkenkamp, 1998). Berkenkamp also describe how DNA and RNA samples can be analyzed by limited sample purification using MALDI-TOF IR.

In Japanese Patent No. 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg.

F. Energy Transfer

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster, 1948. The distance between donor and acceptor dyes at which energy transfer efficiency is 50% is referred to as the Forster distance ($R_o$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Several formats for FET hybridization assays are reviewed in Nonisotopic DNA Probe Techniques (1992. Academic Press, Inc., pgs. 311–352).

Homogeneous methods employing energy transfer or other mechanisms of fluorescence quenching for detection of nucleic acid amplification have also been described. Higuchi, 1992, discloses methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee, 1993, discloses a real-time detection method in which a doubly-labeled detector probe is cleaved in a target amplification-specific manner during PCR™. The detector probe is hybridized downstream of the amplification primer so that the 5'-3' exonuclease activity of Taq polymerase digests the detector probe, separating two fluorescent dyes which form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target.

Signal primers or detector probes which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins.

Many donor/acceptor dye pairs are known in the art and may be used in the present invention. These include, for example, fluorescein isothiocyanate (FITC)/Tetramethylrhodamine isothiocyanate (TALIC), FITC/Texas Red™ (fluorophore) Molecular Probes), FITC/N-hydroxysuccmimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/Tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pair which produces fluorescence quenching in the detector nucleic acids of the invention are suitable for use in the methods of the invention, regardless of the mechanism by which quenching occurs. Terminal and internal labeling methods are both known in the art and maybe routinely used to link the donor and acceptor dyes at their respective sites in the detector nucleic acid.

G. Chip Technologies

Specifically contemplated by the present inventors are chip-based DNA technologies such as those described by Hacia et al., 1996 and Shoemaker et al., 1996. These techniques involve quantitative methods for analyzing large numbers of genes rapidly and accurately. By tagging genes with oligonucleotides or using fixed probe arrays, one can employ chip technology to segregate target molecules on the basis of high density arrays and screen these molecules on the basis of hybridization, Pease et al., 1994; Fodor et al., 1991.

In the present invention, the inventors contemplate the preparation of a high-density array of COP primers on a chip (or on any other solid surface) and conduct the DNA amplification on this solid-phase.

H. OIA™ (Optical Immunoassay)

The inventor's envision the use of BioStar's OIA™ technology to quantitate the amplified product. OIA™ uses the mirror-like surface of a silicon wafer as a substrate. A thin film optical coating and capture antibody is attached to the silicon wafer. White light reflected through the coating appears as a golden background color. This color does not change until the thickness of the optical molecular thin film is changed.

When a positive sample is applied to the wafer, binding occurs between the ligand and the antibody. When substrate is added to complete the mass enhancement, a corresponding change in color from gold to purple/blue results from the increased thickness in the molecular thin film.

I. Real Time PCR

RNA or DNA may be quantitated using the Real-Time PCR technique (Higuchi, 1992). By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundance of the specific mRNA from which the target sequence was derived can be determined for the respective tissues or cells. This direct proportionality between the concentration of the PCR products and the relative mRNA abundance is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundance of a RNA or DNA species can be determined by Real-Time PCR for a collection of RNA or DNA populations is that the concentrations of the amplified PCR products must be sampled when the PCR reactions are in the linear portion of their curves.

The second condition that must be met for an RT-PCR experiment to successfully determine the relative abundance of a particular mRNA species is that relative concentrations of the amplifiable cDNAs must be normalized to some independent standard. The goal of a real-time PCR experiment is to determine the abundance of a particular RNA or DNA species relative to the average abundance of all RNA or DNA species in the sample.

J. Luminex

The Luminex technology allows the quantitation of nucleic acid products immobilized on color coded microspheres. The magnitude of the biomolecular reaction is measured using a second molecule called a reporter. The reporter molecule signals the extent of the reaction by attaching to the molecules on the microspheres. As both the microspheres and the reporter molecules are color coded, digital signal processing allows the translation of signals into real-time, quantitative data for each reaction.

K. Identification Methods

Amplification products must be visualized in order to confirm amplification of the target-gene(s) sequences. One typical visualization method involves staining of a gel with for example, a fluorescent dye, such as ethidium bromide or Vistra Green and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly, using a nucleic acid probe. Following separation of amplification products, a labeled, nucleic acid probe is brought into contact with the amplified gene(s) sequence. The probe preferably is conjugated to a chromophore but may be radiolabeled. In another embodiment, the probe is conjugated to a binding partner, such as an antibody or biotin, where the other member of the binding pair carries a detectable moiety. In other embodiments, the probe incorporates a fluorescent dye or label. In yet other embodiments, the probe has a mass label that can be used to detect the molecule amplified. Other embodiments also contemplate the use of Taqman™ (thermophilic DNA polymerase) and Molecular Beacon™ (hybridization probes) probes. In still other embodiments, solid-phase capture methods combined with a standard probe may be used as well.

The type of label incorporated in PCR™ products is dictated by the method used for analysis. When using capillary electrophoresis, microfluidic electrophoresis, HPLC, or LC separations, either incorporated or intercalated fluorescent dyes are used to label and detect the PCR™ products. Samples are detected dynamically, in that fluorescence is quantitated as a labeled species moves past the detector. If any electrophoretic method, BPLC, or LC is used for separation, products can be detected by absorption of UV light, a property inherent to DNA and therefore not requiring addition of a label. If polyacrylamide gel or slab gel electrophoresis is used, primers for the PCR™ can be labeled with a fluorophore, a chromophore or a radioisotope, or by associated enzymatic reaction. Enzymatic detection involves binding an enzyme to primer, e.g., via a biotin:avidin interaction, following separation of PCR™ products on a gel, then detection by chemical reaction, such as chemiluminescence generated with luminol. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analyzed more than once by probing, stripping the blot, and then reprobing. If PCR™ products are separated using a mass spectrometer no label is required because nucleic acids are detected directly.

A number of the above separation platforms can be coupled to achieve separations based on two different properties. For example, some of the PCR™ primers can be coupled with a moiety that allows affinity capture, and some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affinity chromatography column. The flow-through fraction is collected, and the bound fraction eluted (by chemical cleavage, salt elution, etc.). Each sample is then further fractionated based on a property, such as mass, to identify individual components.

L. Analysis of Data

Gathering data from the various analysis operations will typically be carried out using methods known in the art For example, microcapillary arrays may be scanned using lasers to excite fluorescently labeled targets that have hybridized to regions of probe arrays, which can then be imaged using charged coupled devices ("CCDs") for a wide field scanning of the array. Alternatively, another particularly useful method for gathering data from the arrays is through the use of laser confocal microscopy which combines the ease and speed of a readily automated process with high resolution detection. Scanning devices of this kind are described in U.S. Pat. Nos. 5,143,854 and 5,424,186.

Following the data gathering operation, the data will typically be reported to a data analysis operation. To facilitate the sample analysis operation, the data obtained by a reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of hybridizing probes, normalization of background and single base mismatch hybridizations, ordering of sequence data in SBH applications, and the like, as described in, e.g., U.S. Pat. Nos. 4,683,194, 5,599,668 and 5,843,651 incorporated herein by reference.

M. Kits

The materials and reagents required for detecting and quantitating gene expression from a biological sample may be assembled together in a kit. The kits of the invention generally will comprise a set of restriction endonucleases used to digest the cDNA. Preferred kits will comprise frequent cutters such as four-base cutter, five base cutter or six base cutter restriction enzymes.

The kits of the invention also will generally comprise one or more preselected primer sets and/or probes that may be either specific or non-specific for the genes to be amplified. Preferably, the kits will comprise, in suitable container means, one or more nucleic acid probes and/or primer sets and means for detecting nucleic acids. In certain embodiments, such as in kits for use in amplification reactions, the means for detecting the nucleic acids may be a label, such as a fluorophore, a radiolabel, an enzyme tag, etc., that is linked to the nucleic acid primer or the nucleotides themselves. It is envisioned that kits may contain pairs of primers for standardization of RAGEtag fragment libraries. They will also contain ligase and labeled and unlabeled oligonucleotide linkers.

Preferred kits are those suitable for use in PCR™. In PCR™ kits, two primers will preferably be provided that have sequences from, and that hybridize to, spatially distinct regions of the target gene. Preferred pairs of primers will have two parts, a first subsequence, corresponding to a recognition-sequence of a four-base cutter and a second subsequence, corresponding to a specificity region designed to amplify any possible combination of nucleotides adjacent to the restriction site. Kits of this embodiment will be used to amplify all genes, unknown and/or known, that respond to certain treatments or stimuli. In other embodiments, the second subsequence following the restriction-enzyme sequence will correspond to a known gene or set of genes. The kits of this embodiment will be used to detect and quantitate all known genes that belong to a family or all known genes that respond to a treatment or stimulus. Other preferred pairs of primers for amplifying nucleic acids are selected to amplify the sequences specified herein. Also included in PCR™ kits may be enzymes suitable for amplifying nucleic acids, including various polymerases (RT, Taq, etc.), deoxynucleotides and buffers to provide the necessary reaction mixture for amplification.

The kits of the present invention, although containing at least one sequence corresponding to a restriction-enzyme recognition sequence, as disclosed herein, also may contain one or more of a variety of other target-gene sequences as described above. The kits of the present invention may also include the anchorable moiety, components necessary for second strand cDNA synthesis, linkers, ligase, and kinase.

In each case, the kits will preferably comprise distinct containers for each individual reagent and enzyme, as well as for each probe or primer pair. Each biological agent will generally be suitable aliquoted in their respective containers. The container means of the kits will generally include at least one vial or test tube. Flasks, bottles and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions may be provided with the kit.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Embodiments

FIG. 1 demonstrates a representative illustration of four genes, Mln62, S5, IL-8 and survivin, having differing sizes and restriction patterns. The Mln62 and S5 genes can be analyzed using an "A/B orientation" RAGEtag fragment library, which refers to the order of the restriction digests. Approximately one half of genes can be analyzed using an A/B RAGEtag fragment library, whereas it is necessary to reverse the order of the digestion enzymes and generate a B/A RAGEtag fragment library to analyze the other half of a genome. IL-8 and survivin represent genes that may be analyzed from B/A orientation RAGEtags. The resulting RAGEtag fragment that will be isolated from the cDNA is indicated by the thick gray rectangle.

The 3 end of the genes are shown containing the poly dAn/dTn sequence. In the first step of making a RAGEtag, cDNA is synthesized using a biotinylated oligo dT. The biotin group acts as an anchor to facilitate purification of the desired RAGEtag fragment.

In a proportion of genes one or multiple recognition sites for the second restriction enzyme exist 3' to the restriction site that is proximal to the first restriction enzyme recognition site and generates the desired RAGEtag fragment (FIGS. 1 and 2A). In the original protocol these A/A or B/B fragments are co-purified along with the desired RAGEtags (FIG. 2B). True RAGEtags can only be amplified if A and B primers are present in the mix (FIG. 2C). In cases where the A/A or B/B fragment is abundant, it can be artifactually amplified during PCR by priming with a single primer (FIG. 2D). As a result, PCR products can be generated that are not the result of amplification of RAGEtags.

Figure 3:
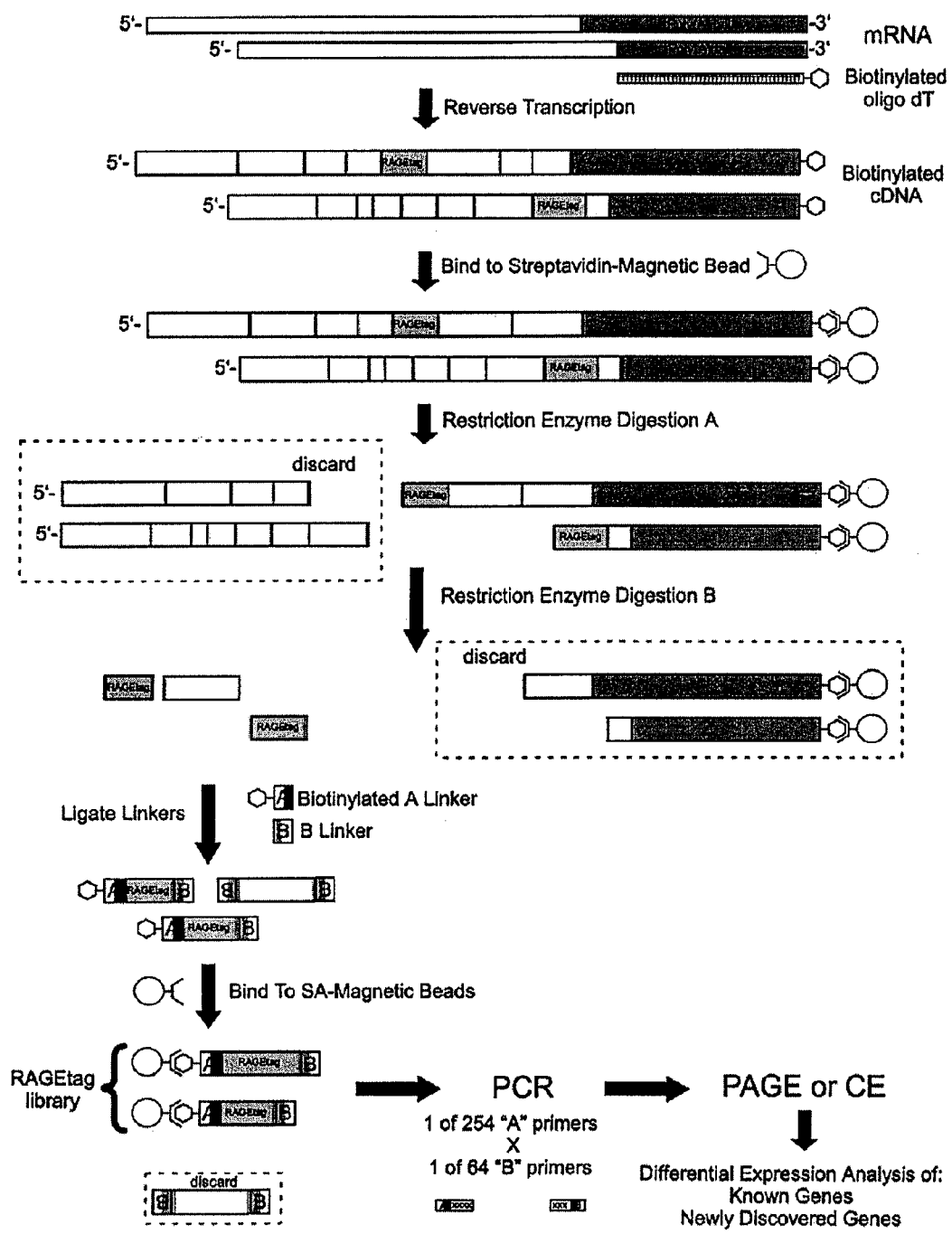
FIG. 3 depicts the protocol for isolation of the RAGEtag fragment library. cDNA is prepared from an mRNA sample using a biotinylated oligo(dT) primer and the cDNA is immobilized on a streptavidin magnetic bead. Two restriction enzymes which cleave DNA leaving unique overhanging "sticky" ends, designated "A" and "B", are used sequentially to fragment the cDNA, and the positions of recognition sites for these enzymes in each cDNA define the position of the RAGEtag for each gene. Two arbitrary genes are diagrammed in the Figure with "A" restriction sites indicated as dark gray bars and "B" restriction sites indicated as light gray bars. Initially, the immobilized cDNAs are cleaved with enzyme "A", leaving only the 3'-most "A" fragment attached to the beads, and the cleaved 5'-fragments are washed off and discarded. The RAGEtag is then cleaved from the beads with enzyme "B", along with other 3'-fragments, and collected. At this point in the preparation, only the RAGEtags contain sticky ends derived from enzyme A; the other fragments of cDNA that contaminate the preparation have "B" sites at both ends. Taking advantage of the unique "sticky" ends left by the "A" and "B" enzymes, the RAGEtags are then ligated to two unique linkers that distinguish the "A" and "B" ends; these provide common "A" and "B" primer binding sites for subsequent PCR analysis; currently used linkers are 19 nt in length. The "A" end linker is biotinylated so that the RAGEtags can be purified in the next step by binding to streptavidin magnetic beads, eliminating the unwanted cDNA fragments that contain only "B" ends.

In order to remove these A/A or B/B fragments from the RAGEtag preparation the protocol as, for example, described in U.S. Pat. No. 6,221,600 was modified (FIG. 3). Either A/B or B/A RAGEtag fragment libraries are generated as follows. The restriction digestions are performed in series. This is followed by ligation of both linkers to the restriction fragments. The linker that will ligate to the restriction cut site generated by the first enzyme has a biotin or other modified group at its 5' end (*A or *B). After simultaneous ligation of the linkers, the resulting ligated *A/B or *B/A fragments are purified out of solution using streptavidin magnetic beads. This ensures that only RAGEtags with A/B or B/A ends are present in the fragment library that will serve as the template for PCR.

These modifications to the protocol speed up the entire process. Use of the anchorable linkers increases the recovery of desired A/B and B/A RAGEtag fragments and enhances the sensitivity to detect rare messages. The anchorable linkers eliminate the need for phenol/chloroform extractions as well as some ethanol precipitations. The current invention allows the entire process to be automated on a robotic liquid handling system, such as the Biomek FX (Beckman, Calif.).

Figure 2:
FIGS. 2A through 2D show a schematic of RAGEtags and restriction fragments resulting from a restriction enzyme digestion with a single A restriction enzyme, a single B restriction enzyme, or both A and B restriction enzymes. The dark area represents the gene specific fragment. The clear area containing sequence represents the linker sequences. The alignment of primers is shown in the boxed (A primer) and shaded (B primer) arrows.
Figure 2:
Figure 2:
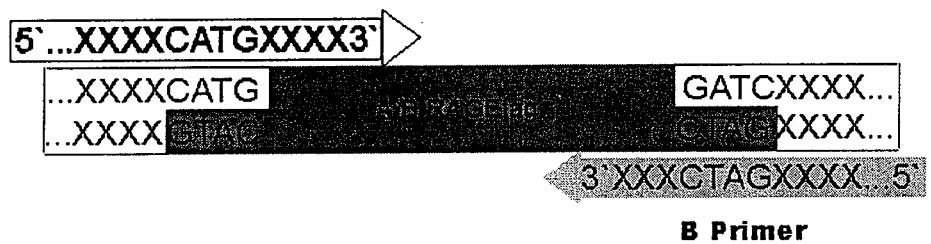
Figure 2:
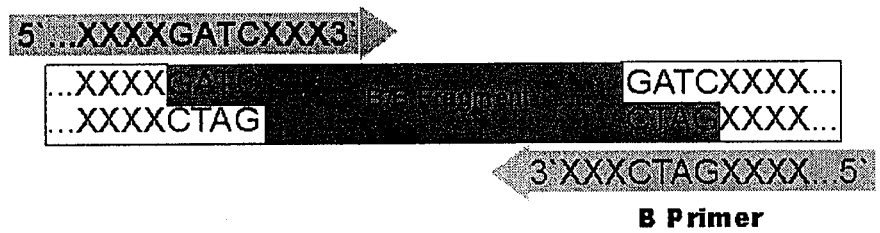

FIG. 2 illustrates generation of RAGEtags from a single or double restriction enzyme digest. The RAGEtags generated by a double restriction enzyme digest require two different primers for amplification by PCR, as opposed to the amplification of fragments which can occur with a single primer, as with other methods in the art.

Example 2

PCR Amplification and Page Analysis

Figure 4:
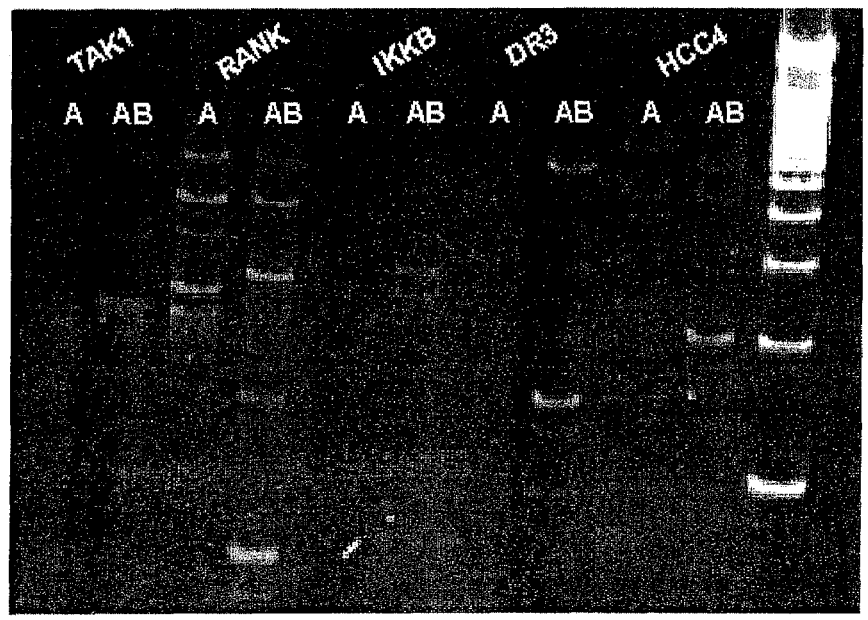
FIGS. 4A through 4B demonstrate PAGE analysis of PCR products using combinatorial oligonucleotide PCR, wherein at least some restriction fragments comprise two identical ends, and a method described herein, wherein the restriction fragment for amplification comprises nonidentical ends.
Figure 4:
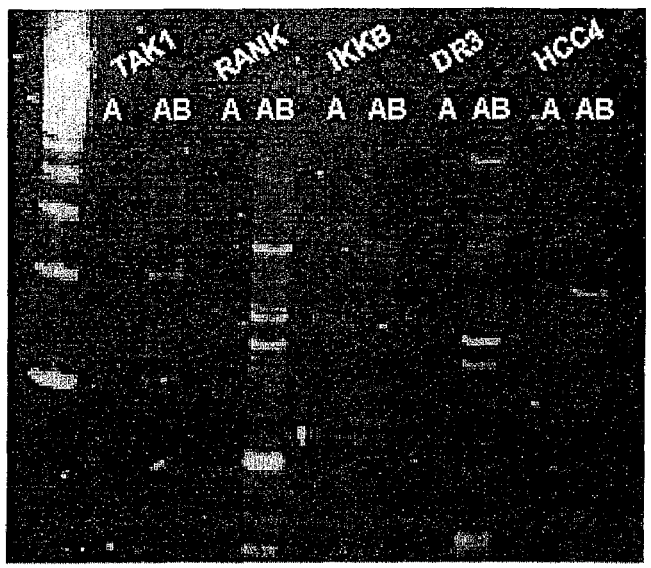

The purpose of the following experiment was to determine whether the modified protocol would eliminate aberrant PCR resulting from priming with a single primer on a restriction fragment that had two "A" ends. A B/A RAGEtag fragment library was prepared using the original protocol (FIG. 4A) and the modified protocol (FIG. 4B) that incorporates a biotinylated A linker. PCR was carried out with both samples. PCR reactions contained either just A primer or both A and B primers. Using the original protocol, PCR products were detected in reactions with A (FIG. 4A lanes 3, 7, 9) and A+B primers (FIG. 4A, lanes 2, 4, 6, 8, 10). In the modified protocol PCR products were only detected in reactions containing both primers (FIG. 4B, lanes 3, 5, 7, 9, 11). Therefore, the modified protocol results in RAGEtags that are not contaminated by restriction fragments resulting from a single restriction enzyme digestion and the resulting aberrant PCR products are eliminated.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents

U.S. Pat. No. 5,053,336, issued October 1991 to Vanderlaan et al.
U.S. Pat. No. 5,290,677 issued March 1994 to Robertson et al.
U.S. Pat. No. 5,521,084 issued May. 1996 to Kowalski et al.
U.S. Pat. No. 5,656,470 issued August 1997 to Martinis et al.
U.S. Pat. No. 5,688,648 issued November 1997 to Mathies et al.
U.S. Pat. No. 5,736,330 issued April 1998 to Fulton
U.S. Pat. No. 5,767,288 issued June 1998 to Rock et al.
U.S. Pat. No. 5,770,716 issued June 1998 to Khan et al.
U.S. Pat. No. 5,804,380 issued September 1998 to Harley et al.
U.S. Pat. No. 5,817,462 issued October 1998 to Garini et al.
U.S. Pat. No. 5,837,836 issued November 1998 to Friderici et al.
U.S. Pat. No. 5,843,773 issued December 1998 to Shin et al.
U.S. Pat. No. 5,851,772 issued December 1998 to Mirzabekov et al.
U.S. Pat. No. 5,853,992 issued December 1998 to Glazer et al.
U.S. Pat. No. 5,866,330 issued February 1999 to Kinzler et al.
U.S. Pat. No. 5,871,697 issued February 1999 to Rothberg et al.
U.S. Pat. No. 5,874,215 issued February 1999 to Kuiper et al.
U.S. Pat. No. 5,945,290 issued August 1999 to Cowsert
U.S. Pat. No. 6,002,817 issued December 1999 to Kopelman et al.
U.S. Pat. No. 6,007,996 issued December 1999 to McNamara et al.
U.S. Pat. No. 6,221,600 issued April 2001 to MacLeod et al.
0 534 858 A1 September, 1992 EP.
WO 98/08981 March, 1998 WO.

PUBLICATIONS

Chen, Z. J., Shen H. and Tew, K. D. 2001. NAR. Gene expression profiling using a novel method: amplified differential gene expression (ADGE).
DeAngelis M M, Wang D G, Hawkins T L. 1995. NAR. 23:4742–3. Solid-phase reversible immobilization for the isolation of PCR products.
Hawkins TL, O'Connor-Morin T, Roy A, Santillan C. 1994. NAR. 22:4543–4. DNA purification and isolation using a solid-phase.
Jiang, H., Kang, D. C., Alexandre, D. and Fisher, P. B. 2000. PNAS. 97:12684–12689. RaSH, a rapid subtraction hybridization approach for identifying and cloning differentially expressed genes.
Kang D C, LaFrance R, Su Z Z, Fisher P B. 1998. Proc Natl Acad Sci USA 95:13788–93. Reciprocal subtraction differential RNA display: an efficient and rapid procedure for isolating differentially expressed gene sequences.
Kornmann, B., Preitner, N., Fleury-Plelea, F. and Schibler, U. 2001. NAR. 29: E51. Analysis of circadian liver gene expression by ADDER, a highly sensitive method for the display of differentially expressed mRNAs.

Lakhani S R, Ashworth A. 2001. Nature Rev Cancer 2001 1:151–7. Microarray and histopathological analysis of tumours: the future and the past?

Schibler, U., Rifat, D., Lavery, D J. 2001. Methods 24:3–14. The Isolation of differentially expressed mRNA sequences by selective amplification via biotin and restriction-mediated enrichment.

Skowronski E W, Armstrong N, Andersen G, Macht M, McCready P M. 2000. Biotechniques 29:786–8, 790, 792. Magnetic, microplate-format plasmid isolation protocol for high-yield, sequencing-grade DNA.

Wang A, Pierce A, Judson-Kremer K, Gaddis S, Aldaz C M, Johnson D G, MacLeod M C. 1999. NAR. 27:4609–18. Rapid analysis of gene expression (RAGE) facilitates universal expression profiling.

One skilled in the art readily appreciates that the present invention is well adapted to carry out the objectives and obtain the ends and advantages mentioned as well as those inherent therein. Particles, compositions, treatments, methods, kits, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

---

We claim:

1. A method, comprising:
   a) obtaining a DNA attached to an anchor;
   b) cleaving said DNA with a first restriction endonuclease ("A") to release restriction fragments therefrom;
   c) removing said released fragments while retaining said cleaved DNA using the anchor;
   d) cleaving said retained DNA with a second restriction endonuclease ("B") different from said first endonuclease, wherein said cleaving results in releasing a fragment mixture comprising:
      i) A/B fragments having nonidentical A and B restriction sites on opposing ends; and
      ii) B/B fragments having the same B restriction sites on opposing ends; and
   e) separating said A/B fragments from said B/B fragments by a method that comprises:
      i) ligating said fragment mixture with A linkers recognizing and binding said A restriction site and B linkers recognizing and binding said B restriction sites, wherein said A linkers are attached to an anchor, and said B linkers are not attached to such an anchor;
      ii) retaining said A/B fragments by immobilizing fragments using the anchor on the A linkers; and
      iii) discarding fragments that have not been immobilized.

2. The method of claim 1, wherein retaining the A/B fragments comprises isolating said fragments.

3. The method of claim 1, wherein retaining the A/B fragments is defined as binding the A/B fragments to a bead.

4. The method of claim 3, wherein said anchor is biotin and wherein said bead is coated with streptavidin.

5. The method of claim 1, wherein said DNA is immobilized using said anchor.

6. The method of claim 5, wherein said DNA is immobilized on a magnetic bead.

7. The method of claim 5, wherein said DNA is immobilized on a magnetic bead through a biotin label, wherein the bead further comprises a coating of streptavidin.

8. The method of claim 1, wherein the ligation of A linkers and B linkers occur concomitantly.

9. The method of claim 1, further comprising amplifying sequences from said A/B fragments.

10. The method of claim 9, wherein said amplification is by polymerase chain reaction with two different primers, one of said primers being complementary to a sequence in the A primer and one being complementary to a sequence in the B primer.

11. The method of claim 1, wherein said DNA is non-genomic DNA.

12. The method of claim 1, wherein said DNA is cDNA.

13. The method of claim 1, wherein said DNA is immobilized at the 3' end.

14. The method of claim 12, wherein said cDNA is reverse transcribed from messenger RNA.

15. The method of claim 14, wherein said reverse transcription is initiated at an oligo dT.

16. The method of claim 14, wherein said reverse transcription is initiated at a random hexamer.

17. The method of claim 15, wherein said oligo dT is biotinylated.

18. The method of claim 9, wherein amplification is carried out with a primer set comprising:
   a) a first amplification primer, wherein the 5' sequence of said primer is complementary to an A linker sequence and the 3' sequence comprises a specificity region;
   b) a second amplification primer, wherein the 5' sequence of said primer is complementary to a B linker sequence and the 3' sequence comprises a specificity region.

19. The method of claim 9, wherein the said DNA fragment is preamplified.

20. The method of claim 18, wherein said amplification is performed with an array of combinations of alternate amplification primers.

21. The method of claim 9, further comprising identifying the amplified DNA.

22. The method of claim 21, wherein said identifying is based upon length.

23. The method of claim 21, wherein said identifying is performed by a computer program.

24. The method of claim 9, wherein said amplifying is performed in a multi-well plate.

25. The method of claim 18, wherein the specificity region of the first amplification primer is 3, 4, 5, 6, 7 or 8 base pairs long.

26. The method of claim 18, wherein the specificity region of the second amplification primer is 3, 4, 5, 6, 7 or 8 base pairs long.

27. The method of claim 1, wherein said first or second restriction endonuclease has a four base pair recognition site.

28. The method of claim 1, wherein said first or second restriction endonuclease has a recognition site of five, six, seven or eight base pairs.

29. The method of claim 27, wherein said first or second restriction endonuclease is NlaIII, DpnII, Sau3AI Hsp92II, MboI, NdeII, Bsp1431, Tsp509 I, HhaI, HinP1I, HpaII, MspI, Taqalphal, MaeII or K2091.

30. The method of claim 9, wherein a label is incorporated into said amplified DNA.

31. The method of claim 30, wherein said label is incorporated by means of a labeled primer.

32. The method of claim 31, further comprising partial nucleotide sequence identification of the amplified products by the identity of the label.

33. The method of claim 32, wherein said label is a chromophore.

34. The method of claim 32, wherein said label is a fluorophore.

35. The method of claim 32, wherein said label is an affinity label.

36. The method of claim 32, wherein said label is a dye.

37. The method of claim 32, wherein the 5' end of said primer comprises an amino moiety and a fluorophore which is covalently attached by the reaction of a succinimido ester of the fluorophore to the 5' amino-modified primer.

38. The method of claim 34, wherein said fluorophore is Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, or Texas Red.

39. The method of claim 9, wherein the products of said amplification are analyzed.

40. The method of claim 39, wherein said analysis of amplification products is by polyacrylamide gel electrophoresis.

41. The method of claim 39, wherein said analysis of amplification products is by capillary gel electrophoresis.

42. The method of claim 39, wherein said analysis of amplification products is by mass spectrophotometry.

43. The method of claim 39, wherein said analysis of amplification products is by energy transfer.

44. The method of claim 39, wherein said analysis of amplification products is by optical immunoassay technology.

45. The method of claim 39, wherein said analysis of amplification products utilizes fluorescently-labeled latex beads.

46. The method of claim 39, wherein said analysis of amplification products comprises quantifying amplification products.

47. The method of claim 46, wherein said quantifying is by measuring the ratio of each amplified product to a co-amplified reference-gene.

48. The method of claim 46, wherein said quantifying is by measuring the ratio of each amplified product to a panel of co-amplified reference-genes.

49. The method of claim 39, wherein said analysis of amplification products is by Real-Time PCR™ (polymerase chain reaction).

50. The method of claim 39, wherein said analysis of amplification products is performed in a multi-well plate.

51. The method of claim 39, wherein said analysis of amplification products is performed on a membrane.

52. The method of claim 39, wherein said analysis of amplification products is performed on a solid matrix.

53. The method of claim 52, wherein said solid matrix is a DNA chip.

54. The method of claim 1, performed on DNA derived from a normal cell or tissue and on DNA derived from a different cell or tissue.

55. The method of claim 1, performed on DNA derived from a normal cell or tissue and on DNA derived from a cancerous cell or tissue.

56. The method of claim 1, performed on DNA derived from a normal cell or tissue and on DNA derived from a cell or tissue treated with a pharmaceutical compound.

57. The method of claim 1, performed on DNA derived from a normal cell or tissue and on DNA derived from a cell or tissue treated with a teratogenic compound.

58. The method of claim 1, performed on DNA derived from a normal cell or tissue and on DNA derived from a cell or tissue treated with a carcinogenic compound.

59. The method of claim 1, performed on DNA derived from a normal cell or tissue and on DNA derived from a cell or tissue treated with a toxic compound.

60. The method of claim 1, performed on DNA derived from a normal cell or tissue and on DNA derived from a cell or tissue treated with a biological response modifier.

61. The method of claim 1, performed on DNA derived from a normal cell or tissue and on DNA derived from a cell or tissue treated with a hormone, a hormone agonist or a hormone antagonist.

62. The method of claim 1, performed on DNA derived from a normal cell or tissue and on DNA derived from a cell or tissue treated with a cytokine.

63. The method of claim 1, performed on DNA derived from a normal cell or tissue and on DNA derived from a cell or tissue treated with a growth factor.

64. The method of claim 1, performed on DNA derived from a normal cell or tissue and on the DNA derived from a cell or tissue treated with the ligand of a known biological receptor.

65. The method of claim 1, performed on DNA derived from a cell or tissue type obtained from a different species.

66. The method of claim 1, performed on DNA derived from a cell or tissue type obtained from a different organism.

67. The method of claim 1, performed on DNA derived from a cell or tissue at different stages of development.

68. The method of claim 1, performed on DNA derived from a normal cell or tissue and on the DNA derived from a cell or tissue that is diseased.

69. The method of claim 1, performed on DNA derived from a cell or tissue cultured in vitro under different conditions.

70. The method of claim 1, performed on the DNA derived from a cell or tissue from two organisms of the same species with a known genetic difference.

* * * * *